US011344487B2

(12) United States Patent
Batista et al.

(10) Patent No.: US 11,344,487 B2
(45) Date of Patent: May 31, 2022

(54) PHOTOPROTECTIVE COMPOSITIONS COMPRISING A DIBENZOYLMETHANE DERIVATIVE, A MEROCYANINE COMPOUND AND A COMPOUND CAPABLE OF ACCEPTING THE TRIPLET EXCITED LEVEL ENERGY OF THE DIBENZOYLMETHANE COMPOUND

(71) Applicant: L'Oreal, Paris (FR)

(72) Inventors: Alexandra Batista, Chevilly-Larue (FR); Didier Candau, Chevilly-Larue (FR); Angelina Roudot, Chevilly-Larue (FR); Mahassine Safouane, Chevilly-Larue (FR); Julie Grumelard, Village-Neuf (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 16/627,177

(22) PCT Filed: Jun. 28, 2018

(86) PCT No.: PCT/EP2018/067472
§ 371 (c)(1),
(2) Date: Dec. 27, 2019

(87) PCT Pub. No.: WO2019/002495
PCT Pub. Date: Jan. 3, 2019

(65) Prior Publication Data
US 2020/0138684 A1 May 7, 2020

(30) Foreign Application Priority Data
Jun. 29, 2017 (FR) ...................... 1756014

(51) Int. Cl.
*A61K 8/35* (2006.01)
*A61K 8/06* (2006.01)
*A61K 8/44* (2006.01)
*A61K 8/49* (2006.01)
*A61Q 17/04* (2006.01)

(52) U.S. Cl.
CPC ............... *A61K 8/35* (2013.01); *A61K 8/062* (2013.01); *A61K 8/064* (2013.01); *A61K 8/44* (2013.01); *A61K 8/4926* (2013.01); *A61Q 17/04* (2013.01); *A61K 2800/522* (2013.01)

(58) Field of Classification Search
CPC .............. A61K 8/44; A61K 8/35; A61K 8/37; A61K 2800/52; A61K 2800/592; A61K 2800/522; A61K 8/064; A61K 8/4926; A61Q 17/04
See application file for complete search history.

(56) References Cited

U.S. PATENT DOCUMENTS

| | | | |
|---|---|---|---|
| 5,993,789 A | 11/1999 | Bonda et al. | |
| 2006/0104924 A1* | 5/2006 | Candau ............... | A61K 8/4926 424/59 |
| 2014/0294743 A1 | 10/2014 | Richard et al. | |
| 2015/0366769 A1* | 12/2015 | Roudot ............... | A61K 8/4946 424/60 |

FOREIGN PATENT DOCUMENTS

| | | |
|---|---|---|
| EP | 1649900 A2 | 4/2006 |
| FR | 2949328 * | 3/2011 |
| FR | 2949328 A1 * | 3/2011 |
| WO | 03007906 A1 | 1/2003 |
| WO | 03103622 A1 | 12/2003 |
| WO | WO 003103622 * | 12/2003 |

OTHER PUBLICATIONS

International Search Report dated Sep. 13, 2018, issued in corresponding International Application No. PCT/EP2018/067472, filed Jun. 28, 2018, 4 pages.

* cited by examiner

*Primary Examiner* — Genevieve S Alley
(74) *Attorney, Agent, or Firm* — Christensen O'Connor Johnson Kindness PLLC

(57) ABSTRACT

The present invention relates to a photoprotective composition for topical use comprising, in a cosmetically acceptable medium, at least one dibenzoylmethane derivative compound, at least one merocyanine compound and at least one compound capable of accepting the triplet excited level energy of said dibenzoylmethane derivative compound(s). The invention also relates to the use of at least one compound capable of accepting the triplet excited level energy of said dibenzoylmethane derivative compound(s), for photostabilizing with respect to UV radiation a composition comprising at least one dibenzoylmethane derivative compound and at least one merocyanine compound.

11 Claims, No Drawings

PHOTOPROTECTIVE COMPOSITIONS COMPRISING A DIBENZOYLMETHANE DERIVATIVE, A MEROCYANINE COMPOUND AND A COMPOUND CAPABLE OF ACCEPTING THE TRIPLET EXCITED LEVEL ENERGY OF THE DIBENZOYLMETHANE COMPOUND

The present invention relates to a photoprotective composition for topical use comprising, in a cosmetically acceptable medium, at least one dibenzoylmethane derivative compound, at least one merocyanine compound and at least one compound capable of accepting the triplet excited level energy of said dibenzoylmethane derivative compound(s).

The invention also relates to the use of at least one compound capable of accepting the triplet excited level energy of said dibenzoylmethane derivative compound(s), for photostabilizing with respect to UV radiation a composition comprising at least one dibenzoylmethane derivative compound and at least one merocyanine compound.

It is known that light radiation with wavelengths of between 280 nm and 400 nm makes possible browning of the human epidermis and that rays with wavelengths more particularly of between 280 and 320 nm, known under the name of UV-B, cause erythemas and skin burns which may be harmful to the development of natural tanning. For these reasons, as well as for aesthetic reasons, there is a constant demand for means for controlling this natural tanning in order thus to control the colour of the skin; this UV-B radiation should thus be screened out.

It is also known that UV-A rays, with wavelengths between 320 and 400 nm, which cause tanning of the skin, are liable to induce adverse changes therein, in particular in the case of sensitive skin or skin that is continually exposed to solar radiation. UV-A rays cause in particular a loss in the elasticity of the skin and the appearance of wrinkles, resulting in premature skin ageing. Thus, for aesthetic and cosmetic reasons, such as the preservation of the natural elasticity of the skin, for example, more and more people wish to control the effect of UV-A rays on their skin. It is therefore desirable also to screen out UV-A radiation.

With the aim of providing protection of the skin and keratin materials against UV radiation, use is generally made of antisun compositions comprising organic screening agents which are active in the UV-A region and which are active in the UV-B region. The majority of these screening agents are fat-soluble.

In this respect, a particularly efficient family of UV-A screening agents is constituted of dibenzoylmethane derivatives and in particular 4-tert-butyl-4'-methoxydibenzoylmethane, this being because these exhibit a high intrinsic absorption power. These dibenzoylmethane derivatives, which are products that are now well known per se as screening agents that are active in the UV-A range, are described in particular in French patent applications FR-A-2 326 405 and FR-A-2 440 933, and also in European patent application EP-A-0 114 607; 4-tert-butyl-4'-methoxydibenzoylmethane is moreover currently sold under the trade name Parsol 1789® by the company DSM Nutritional Products.

Another family, which is also particularly advantageous, is constituted of lipophilic merocyanine derivatives. These derivatives are known to screen out long-wave UV-A radiation with wavelengths above 370 nm, and are particularly described in U.S. Pat. No. 4,195,999, application WO 2004/006878, document IP COM Journal 4 (4), 16 N°IPCOM000011179D published on Apr. 3, 2004.

However, the applicant has been able to note that combinations of merocyanine derivatives with dibenzoylmethane derivatives have the drawback of being particularly photo-unstable with regard to ultraviolet radiation (especially UV-A radiation). These particular combinations of UV-screening agents degrade more or less rapidly under the action of UV radiation; this degradation being particularly significant for merocyanine derivatives. Thus, this substantial lack of photochemical stability of the combination of merocyanine derivatives with dibenzoylmethane derivatives in the face of the ultraviolet radiation to which this combination is by nature intended to be subjected does not make it possible to guarantee continuous protection during prolonged exposure to the sun, so that repeated applications at regular and close intervals of time have to be carried out by the user in order to obtain effective and long-lasting protection of the skin against UV rays.

There is therefore a real need to photostabilize the combination of merocyanine derivatives with dibenzoylmethane derivatives with respect to UV radiation, in order to guarantee constant protection during prolonged exposure to the sun with respect to UV-A radiation.

However, not all stabilizers of dibenzoylmethane derivatives such as 4-tert-butyl-4'-methoxydibenzoylmethane make it possible to stabilize combinations thereof with merocyanine compounds.

As it happens, the applicant has just recently discovered, surprisingly, that the use of at least one particular compound capable of accepting the triplet excited level energy of said dibenzoylmethane derivative compound(s) makes it possible to substantially improve the photochemical stability (or photostability) of combinations of merocyanine compounds and dibenzoylmethane derivatives, and thus to improve the photoprotective performance levels of compositions containing these two types of sunscreens.

A subject of the present invention is therefore a photoprotective composition for topical use, characterized in that it comprises, in a cosmetically acceptable medium:
 (i) one or more dibenzoylmethane derivative compounds chosen from those of formula (I) below, and/or mixtures thereof:

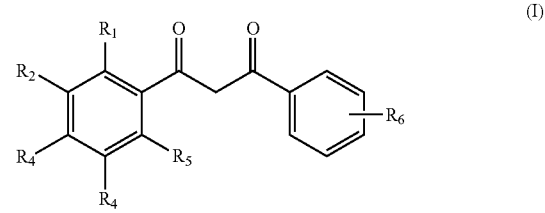

(I)

in which formula (I):
$R_1$, $R_4$, $R_5$ and $R_6$ represent, independently of one another, a hydrogen atom, a hydroxyl radical, a linear or branched $C_1$-$C_4$ alkyl radical or a linear or branched $C_1$-$C_4$ alkoxy radical, and $R_2$ and $R_3$ represent, independently of one another, a hydrogen atom, a hydroxyl radical, a linear or branched $C_1$-$C_4$ alkyl radical or a linear or branched $C_1$-$C_4$ alkoxy radical, or form, with the 2 carbon atoms of the covalent bonds C—$R_2$ and C—$R_3$, a 5- or 6-membered heterocycle optionally substituted with a linear or branched $C_1$-$C_4$ hydrocarbon-based chain;

(ii) one or more merocyanine compounds chosen from those of formula (II) below, the tautomeric forms thereof, the geometric isomers E/E or E/Z thereof; and/or mixture thereof:

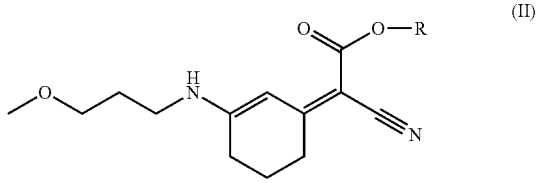

(II)

in which formula (II), R represents a linear or branched $C_1$-$C_{22}$ alkyl, $C_2$-$C_{22}$ alkenyl or $C_2$-$C_{22}$ alkynyl radical, a $C_3$-$C_{22}$ cycloalkyl radical or a $C_3$-$C_{22}$ cycloalkenyl radical, said radicals possibly being interrupted with one or more oxygen atoms; and (iii) one or more compounds capable of accepting triplet excited level energy of said dibenzoylmethane derivative compound(s) (i).

These compositions make it possible to screen out solar radiation efficiently, they are broad-spectrum, in particular for UV-A radiation (including long-wave UV-A radiation), while the same time being particularly stable over time under UV exposure.

These compositions may also in certain cases exhibit an improved sun protection factor or "SPF".

Other subjects, characteristics, aspects and advantages of the invention will emerge even more clearly on reading the description and the examples that follow.

In the text hereinbelow, and unless otherwise indicated, the limits of a range of values are included in that range, in particular in the expressions "between . . . and . . . " and "ranging from . . . to . . . ".

Moreover, the expressions "one or more" and "greater than or equal to" used in the present description are equivalent to the expressions "at least one" and "at least", respectively.

The term "cosmetically acceptable medium" is intended to mean compatible with the skin and/or its integuments, having a pleasant colour, odour and feel and not causing any unacceptable discomfort (stinging, tautness or redness) liable to discourage the consumer from using this composition.

The expressions "optionally substituted" and "substituted or unsubstituted" are intended to mean that the radical or group may be optionally substituted with one or more hydroxyls; amino groups —$NR_1R_2$, such that $R_1$ and $R_2$ represent, independently of one another, hydrogen atoms or $C_1$-$C_3$ alkyl radicals; carboxylic —COOH, carbonyl or $C_1$-$C_4$ alkyl groups.

The Dibenzoylmethane Derivative Compounds

The composition according to the present invention comprises one or more dibenzoylmethane derivatives chosen from those of formula (I) below and/or mixtures thereof:

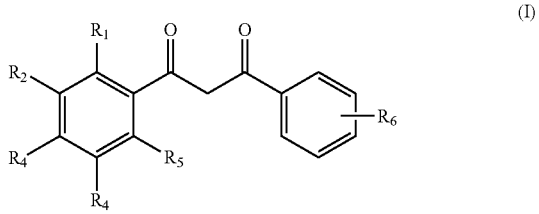

(I)

in which formula (I):

$R_1$, $R_4$, $R_5$ and $R_6$ represent, independently of one another, a hydrogen atom, a hydroxyl radical, a linear or branched $C_1$-$C_4$ alkyl radical or a linear or branched $C_1$-$C_4$ alkoxy radical, and $R_2$ and $R_3$ represent, independently of one another, a hydrogen atom, a hydroxyl radical, a linear or branched $C_1$-$C_4$ alkyl radical or a linear or branched $C_1$-$C_4$ alkoxy radical, or form, with the 2 carbon atoms of the covalent bonds C—$R_2$ and C—$R_3$, a 5- or 6-membered heterocycle optionally substituted with a linear or branched $C_1$-$C_4$ hydrocarbon-based chain.

When $R_2$ and $R_3$ form a heterocycle with the 2 carbon atoms of the covalent bonds C—$R_2$ and C—$R_3$, they preferably form a 5-membered aromatic heterocycle, more preferentially a furan ring.

Preferably, $R_2$ and $R_3$ represent, independently of one another, a hydrogen atom, a hydroxyl radical, a linear or branched $C_1$-$C_4$ alkyl radical or a linear or branched $C_1$-$C_4$ alkoxy radical.

According to one preferred embodiment of the invention, the dibenzoylmethane derivative compound(s) included in the composition according to the invention are chosen, alone or as a mixture, from 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropyldibenzoylmethane, 4,4'-dimethoxydibenzoylmethane, 4-tert-butyl-4'-methoxydibenzoylmethane, 2-methyl-5-isopropyl-4'-methoxydibenzoylmethane, 2-methyl-5-tert-butyl-4'-methoxydibenzoylmethane, 2,4-dimethyl-4'-methoxydibenzoylmethane, 2,6-dimethyl-4-tert-butyl-4'-methoxydibenzoylmethane, 1-(4-tert-butylphenyl)-3-(2-hydroxyphenyl)propane-1,3-dione, 1-(4-methoxy-1-benzofuran-5-yl)-3-phenylpropane-1,3-dione; preferably chosen, alone or as a mixture, from 4-tert-butyl-4'-methoxydibenzoylmethane and/or 4-isopropyldibenzoylmethane; preferentially chosen from 4-tert-butyl-4'-methoxydibenzoylmethane.

By way of example, 4-isopropyldibenzoylmethane is sold under the name Eusolex 8020 by the company Merck, and 4-tert-butyl-4'-methoxydibenzoylmethane or butyl-methoxydibenzoylmethane is sold under the name Parsol 1789 by the company Roche Vitamins.

By way of example, likewise, 1-(4-methoxy-1-benzofuran-5-yl)-3-phenylpropane-1,3-dione is sold under the name Pongamol by the company Quest, of formula:

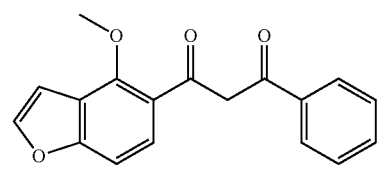 [SMILES: COc1c(C(=O)CC(=O)c2ccccc2)ccc2occc12]

Preferably, the total content of the dibenzoylmethane derivative compound(s) (I) present in the composition is between 0.1% and 15% by weight, preferably between 0.2% and 10% by weight, more preferentially between 0.3% and 5% by weight, relative to the total weight of the composition.

The Merocyanine Compounds

The composition according to the present invention comprises one or more merocyanine compounds chosen from those of formula (II) below, the tautomeric forms thereof, the geometric isomers E/E or E/Z thereof; and/or mixtures thereof:

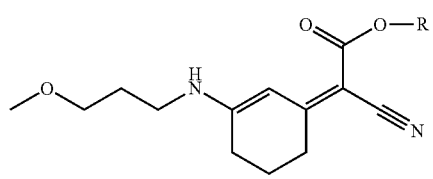
(II)

in which formula (II), R represents a linear or branched $C_1$-$C_{22}$ alkyl, $C_2$-$C_{22}$ alkenyl or $C_2$-$C_{22}$ alkynyl radical, a $C_3$-$C_{22}$ cycloalkyl radical or a $C_3$-$C_{22}$ cycloalkenyl radical, said radicals possibly being interrupted with one or more oxygen atoms.

As indicated above, the merocyanine compounds of the invention may be present in their geometric isomer forms E/E, E/Z, and/or mixtures of these two types of forms:

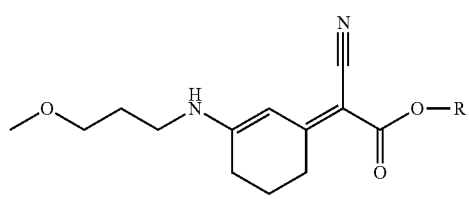

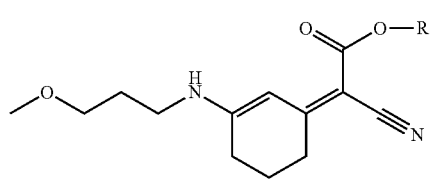

Preferably, the merocyanine compounds of formula (II) have a radical R denoting a linear or branched $C_1$-$C_{22}$ alkyl radical which may be interrupted with one or more oxygen atoms.

According to one preferred embodiment of the invention, the merocyanine compound(s) are chosen from the following compounds (1') to (6'), and also the tautomeric forms thereof, the geometric isomers E/E or E/Z thereof; and/or mixtures thereof:

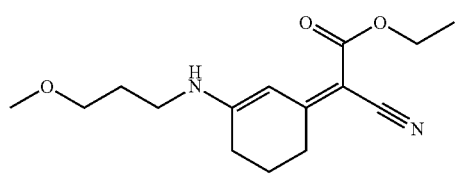
(1')

ethyl 2-cyano{3-[(3-methoxypropyl)amino]cyclohex-2-en-1-ylidene}ethanoate

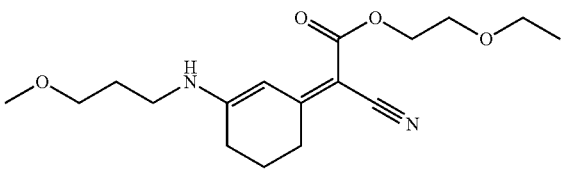
(2')

2-ethoxyethyl 2-cyano{3-[(3-methoxypropyl)amino]cyclohex-2-en-1-ylidene}ethanoate

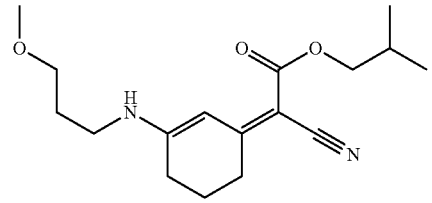
(3')

2-methylpropyl 2-cyano{3-[(3-methoxypropyl)amino]cyclohex-2-en-1-ylidene}ethanoate

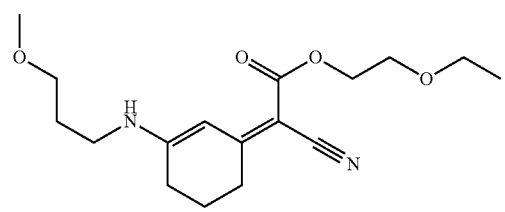
(4')

2-butoxyethyl 2-cyano{3-[(3-methoxypropyl)amino]cyclohex-2-en-1-ylidene}ethanoate

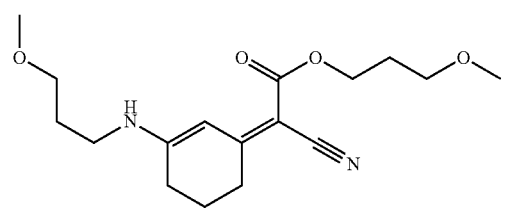
(5')

3-methoxypropyl 2-cyano{3-[(3-methoxypropyl)amino]cyclohex-2-en-1-ylidene}ethanoate

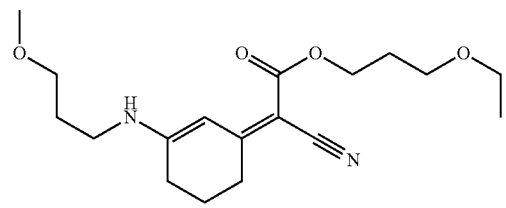
(6')

3-ethoxypropyl 2-cyano{3-[(3-methoxypropyl)amino]cyclohex-2-en-1-ylidene}ethanoate According to a more particularly preferred embodiment of the invention, at least one merocyanine compound is chosen from 2-ethoxyethyl 2-cyano {3-[(3-methoxypropyl)amino] cyclohex-2-en-1-ylidene}ethanoate (2') (INCI name:

methoxypropylamino cyclohexenylidene ethoxyethylcyanoacetate) in its geometric configuration E/Z having the structure below:

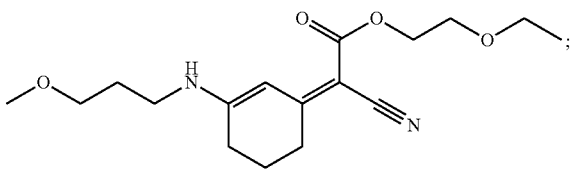 [SMILES: CCOCCOC(=O)/C(C#N)=C1\C=C(NCCCOC)CCC1]

and/or in its geometric configuration E/E having the structure below:

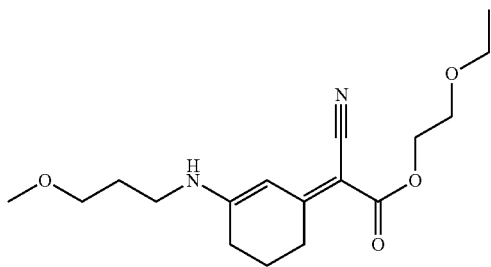 [SMILES: CCOCCOC(=O)/C(C#N)=C1/C=C(NCCCOC)CCC1]

and also the tautomeric forms thereof; and mixtures thereof.

The composition according to the invention preferably comprises said merocyanine compound(s) (ii) in a content of between 0.1% and 10% by weight, preferably between 0.2% and 10% by weight and even more preferentially between 0.3% and 5% by weight, relative to the total weight of the composition.

The compounds of formula (II) may be prepared according to the protocols described in patent application WO 2007/071582, in IP.com Journal (2009), 9(5A), 29-30 IPCOM000182396D under the title "Process for producing 3-amino-2-cyclohexan-1-ylidene compounds" and in U.S. Pat. No. 4,749,643 in col, 13, line 66-col. 14, line 57 and the references cited in this regard.

The Compounds Capable of Accepting the Triplet Excited Level Energy of Said Dibenzoylmethane Derivative Compound(s)

The composition according to the present invention comprises one or more compounds capable of accepting the triplet excited level energy of said dibenzoylmethane derivative compound(s) in such a way as to deactivate the excited states of the dibenzoylmethane molecule excited under the influence of UV radiation and to allow that molecule to return to its fundamental state.

The compounds capable of accepting the triplet excited level energy of said dibenzoylmethane derivative compound(s) may be chosen from:
(a) 4-hydroxybenzylidene malonate derivatives or 4-hydroxycinnamate derivatives such as those described in patent application WO 03/007906, and/or 4-hydroxybenzyl malonate derivatives;
(b) piperidinol salts such as those described in patent application WO 03/103622;
(c) naphthalene derivatives such as those described in U.S. Pat. Nos. 5,993,789, 6,113,931, 6,126,925 and 6,284,916;
(d) ethylhexyl methoxycrylene derivatives; and/or
(e) mixtures thereof.

According to one preferred embodiment of the invention, the compounds capable of accepting the triplet excited level energy of said dibenzoylmethane derivative compound(s) have a triplet excited level energy ranging from 40 kcal/mol to 70 kcal/mol.

The triplet excited level energies can be determined using the techniques of oxygen perturbation or phosphorescence, as described in the article by J. Gonzenbach, T. J. Hill, T. G Truscott The Triplet Energy Levels in UVA and UVB Sunscreens, *J. Photochem. Photobiol. B: Biol*, vol 16, pages 337-379 (1992). The technique of oxygen perturbation consists in measuring the UV absorption spectrum of a compound when the latter is placed in an environment under a high oxygen pressure: i.e. 2000 psi. Under these conditions, the spin selection rules are perturbed and the exposure of the compound to the UV leads to the lowest triplet excited level by direct excitation of the ground state. The wavelength $\lambda$ (in $\mu$m) at which the transition takes place is used to calculate the energy of the triplet level in kcal/mol via the formula $E=28.635/\lambda$ which is derived from the equation $E=h\upsilon$ where E is the energy, h is Planck's constant and $\upsilon$ is the frequency of the electromagnetic wave.

The phosphorescence technique is based on the fact that many compounds emit phosphorescence during the deactivation of their triplet excited level. By measuring the wavelength at which the phosphorescence intervenes, the triplet excited level energies can be calculated as previously. The triplet excited level energies can be determined by measuring the phosphorescence spectra of samples with a spectrophotometer equipped with a phosphorescence accessory. Such triplet excited levels have been widely reported for example in the article by A. J. Gordon, R. A. Ford, *The Chemist Companion*, John Wiley & Sons, pages 351-355 (1992).

Among the 4-hydroxybenzylidene malonate derivatives or the 4-hydroxycinnamate derivatives, use will preferentially be made of those of formula below (III) below, and also the tautomeric forms thereof, the optical isomers thereof, the geometric isomers thereof; and/or mixtures thereof:

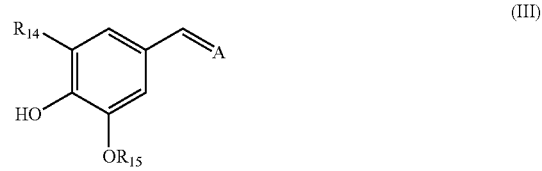

in which:

A is a chromophore group which absorbs UV radiation, comprising two monovalent groups having a carbonyl function;

$R_{14}$ represents a hydrogen atom; a linear or branched $C_1$-$C_8$ alkyl radical; a linear or branched $C_1$-$C_8$ alkoxy radical;

$R_{15}$ denotes a linear or branched $C_1$-$C_8$ alkyl radical.

Among these compounds, use will more preferentially be made of those of formula (IIIa) below, and also the tautomeric forms thereof, the optical isomers thereof, the geometric isomers thereof; and/or mixtures thereof:

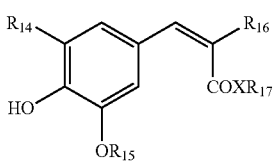

in which
$R_{14}$ represents a hydrogen atom, a linear or branched $C_1$-$C_8$ alkyl radical, or a linear or branched $C_1$-$C_8$ alkoxy radical;
$R_{15}$ represents a hydrogen atom or a linear or branched $C_1$-$C_8$ alkyl radical;
$R_{16}$ is chosen from —C(O)CH$_3$, —CO$_2$R$_{18}$, —C(O)NH$_2$ and —C(O)N(R$_{19}$)$_2$;
X denotes O or NH;
$R_{17}$ represents a linear or branched $C_1$-$C_{30}$ alkyl radical;
$R_{18}$ represents a linear or branched $C_1$-$C_{20}$ alkyl radical;
each $R_{19}$ represents, independently of one another, a linear or branched $C_1$-$C_8$ alkyl radical.

Among these compounds, use will more preferentially be made of those of formula (IIIb) or (IIIc) below, and also the tautomeric forms thereof, the optical isomers thereof, the geometric isomers thereof; and/or mixtures thereof:

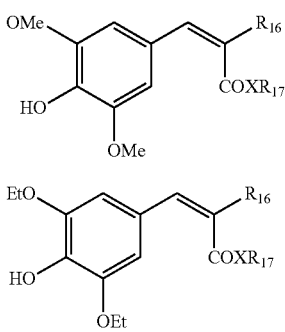

in which:
$R_{16}$ denotes —CO$_2$R$_{18}$;
$R_{17}$ denotes a linear or branched $C_1$-$C_8$ alkyl;
$R_{18}$ denotes a linear or branched $C_1$-$C_8$ alkyl;
X denotes O.

The diethylhexyl syringylidenemalonate compound (INCI name: diethylhexyl syringylidenemalonate) of formula (IV) below will in particular be used:

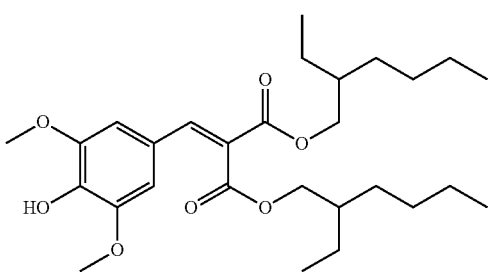

such as the commercial product sold under the trade name Oxynex ST by the company Merck, and also tautomeric forms thereof, the optical isomers thereof, and/or mixtures thereof.

Among the 4-hydroxybenzyl malonate derivatives, use will preferentially be made of those of formula (IIIbis) below, and also the tautomeric forms thereof, the optical isomers thereof, the geometric isomers thereof; and/or mixtures thereof:

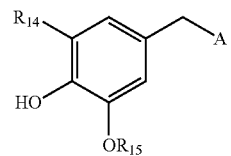

in which:
A is a chromophore group which absorbs UV radiation, comprising two monovalent groups having a carbonyl function;
$R_{14}$ represents a hydrogen atom; a linear or branched $C_1$-$C_8$ alkyl radical; a linear or branched $C_1$-$C_8$ alkoxy radical;
$R_{15}$ denotes a linear or branched $C_1$-$C_8$ alkyl radical.

Among these compounds, use will more preferentially be made of those of formula (IIIbis a) below, and also the tautomeric forms thereof, the optical isomers thereof, the geometric isomers thereof; and/or mixtures thereof:

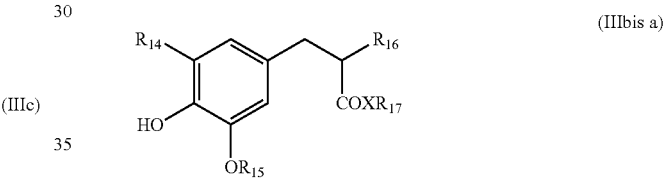

in which
$R_{14}$ represents a hydrogen atom, a linear or branched $C_1$-$C_8$ alkyl radical, or a linear or branched $C_1$-$C_8$ alkoxy radical;
$R_{15}$ denotes a hydrogen atom or a linear or branched $C_1$-$C_8$ alkyl radical;
$R_{16}$ is chosen from —C(O)CH$_3$, —CO$_2$R$_{18}$, —C(O)NH$_2$ and —C(O)N(R$_{19}$)$_2$;
X denotes O or NH;
$R_{17}$ represents a linear or branched $C_1$-$C_{30}$ alkyl radical;
$R_{18}$ represents a linear or branched $C_1$-$C_{20}$ alkyl radical;
each $R_{19}$ represents, independently of one another, a linear or branched $C_1$-$C_8$ alkyl radical.

Among these compounds, use will more preferentially be made of those of formula (IIIbis b) or (IIIbis c) below, and also the tautomeric forms thereof, the optical isomers thereof, the geometric isomers thereof; and/or mixtures thereof:

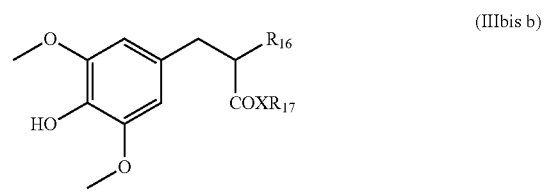

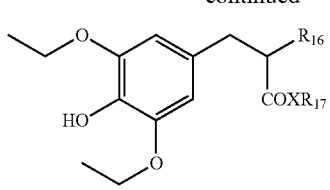
(IIIbis c)

in which:
$R_{16}$ denotes —$CO_2R_{18}$;
$R_{17}$ denotes a linear or branched $C_1$-$C_8$ alkyl;
$R_{18}$ denotes a linear or branched $C_1$-$C_8$ alkyl;
X denotes O.

Use will in particular be made of the compound bis(2-ethylhexyl) 2-[(4-hydroxy-3,5-dimethoxyphenyl)methyl] propanedioate (INCI name: Bis-ethylhexyl hydroxydimethoxy benzylmalonate) of formula (IVbis) below:

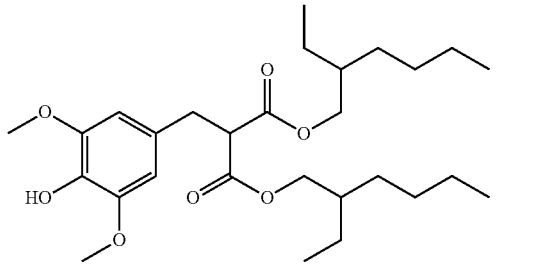
(IVbis)

such as the commercial product sold under the trade name Ronacare AP by the company Merck, and also tautomeric forms thereof, the optical isomers thereof, and/or mixtures thereof.

Among the piperidinol salts in accordance with the invention, use will preferably be made of those of formula (V) below, and also the optical isomers thereof, the geometric isomers thereof; and/or mixtures thereof:

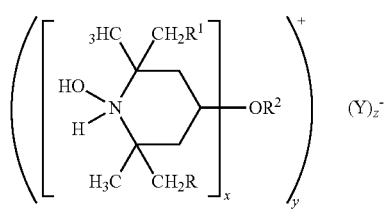
(V)

in which:
R and $R^1$, which may be identical or different, denote a hydrogen atom or a methyl group;
y is 1, 2, 3 or 4;
z is 1, 2, 3 or 4;
x is 1 or 2;
1) when x is equal to 1:
$R^2$ denotes a hydrogen atom; a $C_1$-$C_{18}$ alkyl radical; a $C_2$-$C_{18}$ alkenyl radical; a propargyl radical; a glycidyl group; a $C_2$-$C_{50}$ alkyl radical interrupted with 1 to 20 oxygen atoms and substituted with 1 to 10 hydroxyl groups; a $C_1$-$C_4$ alkyl radical substituted with a carboxy group or a group —COOZ where Z represents a hydrogen atom, a $C_1$-$C_4$ alkyl, a phenyl, a $C_1$-$C_4$ alkyl substituted with a group $(COO^-)_p M^{p+}$ where p is an integer from 1 to 3 and M is a metal ion of groups 1, 2 and 3 of the periodic table, or Zn, Cu, Ni or Co or else M is a group $N^{p+}(R'')_4$ where R'' is a $C_1$-$C_8$ alkyl or a benzyl;
2) when X is 2:
$R^2$ is a $C_1$-$C_{12}$ alkylene radical; a $C_4$-$C_{12}$ alkenylene radical; a xylylene group; a $C_1$-$C_{50}$ alkylene radical interrupted with 1 to 20 oxygen atoms and substituted with 1 to 10 hydroxyl groups;
Y denotes an organic or inorganic anion;
the total charge of cations y being equal to the total charge of anions z.

Among the anions Y, mention may be made of a phosphate, phosphonate, carbonate, bicarbonate, nitrate, chloride, bromide, bisulfite, sulfite, bisulfate, sulfate, borate, formate, acetate, benzoate, citrate, oxalate, tartrate, acrylate, polyacrylate, fumarate, maleate, itaconate, glycolate, gluconate, malate, mandelate, tiglate, ascorbate, polymethacrylate, nitrilotriacetic acid carboxylate, hydroxyethylenediaminetriacetic acid carboxylate, ethylenediaminetetraacetic acid carboxylate, diethylenediaminepentaacetic acid carboxylate, diethylenetriaminepentamethylenephosphonate, alkylsulfonate or an arylsulfonate.

Use will in particular be made of the compounds for which R, $R^1$ and $R^2$ denote a hydrogen atom, x=1 and Y denotes the citrate anion citrate and even more particularly the compound tris(tetramethylhydroxypiperidinol) citrate of formula (VI):

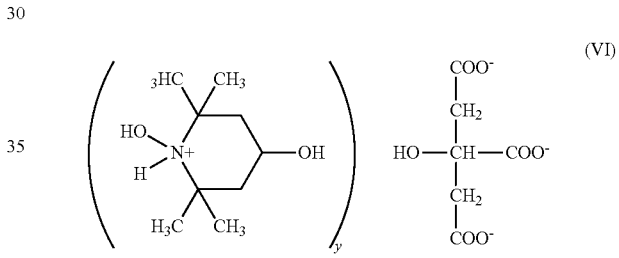
(VI)

with y=3, such as the commercial product sold under the name Tinoguard Q or Tinoguard S-FX by the company Ciba-Geigy, and also tautomeric forms thereof, the optical isomers thereof, and/or mixtures thereof.

Among the naphthalene derivatives in accordance with the invention, use will more particularly be made of the naphthalenedicarboxylic acid diesters and polyesters chosen from
(i) the diesters of formula (VII) below:

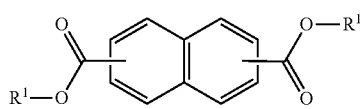
(VII)

(ii) the diesters or the polyesters of formula (VIII) below:

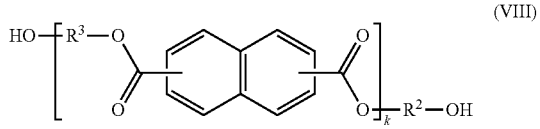
(VIII)

(iii) the diesters or the polyesters blocked with an alcohol of formula (IX) below:

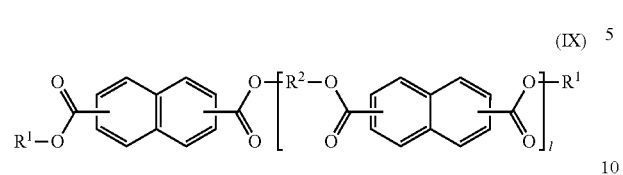

(iv) mixtures thereof;
in which:

the radicals R', which may be identical or different, denote a linear or branched $C_1$-$C_{22}$ alkyl radical;

the radicals $R^2$ and $R^3$, which may be identical or different, denote a linear or branched $C_1$-$C_6$ alkylene radical;

k and l are numbers from 1 to 100, preferably from 1 to 10 and more preferentially from 2 to 7.

Among these naphthalenedicarboxylic acid diesters and polyesters of formula (VII), (VIII) or (IX), use will preferably be made of the 2,6-naphthalenedicarboxylic acid diesters and polyesters.

Among the polyesters corresponding to formula (IX), those resulting from the reaction of 2,6-naphthalenedicarboxylic acid and of tripropylene glycol and blocked with 2-butyloctanol, and also the polyesters resulting from the reaction of 2,6-naphthalene dicarboxylic acid, of tripropylene glycol and of diethylene glycol and blocked with 2-ethylhexanol, will preferably be chosen.

Among the naphthalene derivatives in accordance with the invention, use will preferably be made of diethylhexyl 2,6-naphthalate (INCI name) and also the optical isomers thereof, such as the product sold under the trade name Coropan TQ by the company C.P. HALL.

Among the ethylhexyl methoxycrylene derivatives, use will preferentially be made of those of formula (X) below, and also the optical isomers thereof, the geometric isomers thereof; and/or mixtures thereof:

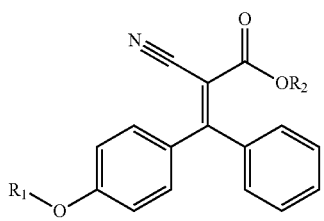

in which:

$R_1$ represents a hydrogen atom or a linear or branched $C_1$-$C_8$ alkyl radical, $R_2$ represents a linear or branched $C_1$-$C_{20}$, preferably $C_1$-$C_8$, alkyl radical.

Use will in particular be made of the compound 2-ethylhexyl-2-cyano-3-(4-methoxyphenyl)-3-phenylprop-2-enoate (INCI name: Ethylhexyl Methoxycrylene) of formula (Xbis) below:

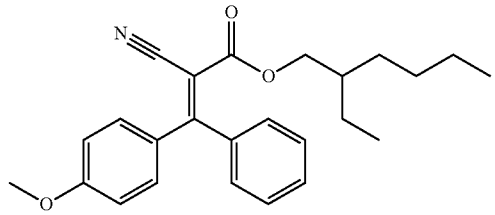

such as the commercial product sold under the trade name Solastay S1 by the company Hallstar, and also tautomeric forms thereof, the optical isomers thereof, and/or mixtures thereof.

Preferably, the total content of the compound(s) (iii) capable of accepting the triplet excited level energy of said dibenzoylmethane derivative compound(s) present in the composition is between 0.001% and 15% by weight, preferably between 0.003% and 10% by weight, and more preferentially between 0.005% and 5% by weight, relative to the total weight of the composition.

According to one preferred embodiment of the invention, the compound(s) (iii) capable of accepting the triplet excited level energy of said dibenzoylmethane derivative compound(s) are chosen, alone or as a mixture, from the diethylhexyl syringylidenemalonate of formula (IV) and also the tautomeric forms thereof, the optical isomers thereof, and/or mixtures thereof; the bisethylhexylhydroxydimethoxy benzylmalonate of formula (IVbis) and also the tautomeric forms thereof, the optical isomers thereof, and/or mixtures thereof; the tris(tetramethylhydroxypiperidinol) citrate of formula (VI) and also the optical isomers thereof, and/or mixtures thereof; diethylhexyl 2,6-naphthalate and also the optical isomers thereof; and the ethylhexyl methoxycrylene of formula (Xbis) and also the tautomeric forms thereof, the optical isomers thereof, and/or mixtures thereof.

According to another preferred embodiment of the invention, the ratio of the weight content of the compound(s) (iii) capable of accepting the triplet excited level energy of said dibenzoylmethane derivative compound(s) to the sum of the weight contents of the dibenzoylmethane derivative compound(s) (i) and of the merocyanine compound(s) (ii), is between 0.01 and 20, preferably between 0.1 and 15, more preferentially between 0.5 and 10.

Additional UV-Screening Agents

The composition according to the present invention may optionally comprise one or more additional UV-screening agents chosen from hydrophilic, lipophilic or insoluble organic UV-screening agents and/or one or more mineral pigments. It will preferentially be constituted of at least one hydrophilic, lipophilic or insoluble organic UV-screening agent.

The term "hydrophilic UV-screening agent" is intended to mean any cosmetic or dermatological organic or inorganic compound for screening out UV radiation, which can be fully dissolved in molecular form in a liquid aqueous phase or which can be dissolved in colloidal form (for example in micellar form) in a liquid aqueous phase.

The term "lipophilic screening agent" is intended to mean any cosmetic or dermatological organic or inorganic compound for screening out UV radiation, which can be fully dissolved in molecular form in a liquid fatty phase or which can be dissolved in colloidal form (for example in micellar form) in a liquid fatty phase.

The term "insoluble UV-screening agent" is intended to mean any cosmetic or dermatological organic or inorganic compound for screening out UV radiation which has a solubility in water of less than 0.5% by weight and a solubility of less than 0.5% by weight in the majority of organic solvents such as liquid paraffin, fatty alcohol benzoates and fatty acid triglycerides, for example Miglyol 812® sold by the company Dynamit Nobel. This solubility, determined at 70° C., is defined as the amount of product in solution in the solvent at equilibrium with an excess of solid in suspension after returning to ambient temperature. It may be readily evaluated in the laboratory.

The additional organic UV-screening agents are chosen in particular from cinnamic compounds; anthranilate compounds; salicylic compounds; benzylidenecamphor compounds; benzophenone compounds; β,β-diphenylacrylate compounds different from the ethylhexyl methoxycrylene derivatives; triazine compounds; benzotriazole compounds; benzalmalonate compounds, in particular those cited in U.S. Pat. No. 5,624,663; benzimidazole derivatives; imidazo line compounds; bis-benzazolyl compounds, as described in patents EP 669 323 and U.S. Pat. No. 2,463,264; p-aminobenzoic acid (PABA) compounds; methylenebis(hydroxyphenylbenzotriazole) compounds, as described in patent applications U.S. Pat. Nos. 5,237,071, 5,166,355, GB 2 303 549, DE 197 26 184 and EP 893 119; benzoxazole compounds, as described in patent applications EP 0 832 642, EP 1 027 883, EP 1 300 137 and DE 101 62 844; screening polymers and screening silicones, such as those described in particular in patent application WO 93/04665; α-alkylstyrene-based dimers, such as those described in patent application DE 198 55 649; 4,4-diarylbutadiene compounds, such as those described in patent applications EP 0 967 200, DE 197 46 654, DE 197 55 649, EP-A-1 008 586, EP 1 133 980 and EP 133 981, and mixtures thereof.

As examples of organic photoprotective agents, mention may be made of those denoted hereinbelow under their INCI name:

Cinnamic Compounds:
Ethylhexyl methoxycinnamate sold in particular under the trade name Parsol MCX® by DSM Nutritional Products,
Isopropyl methoxycinnamate,
Isoamyl p-methoxycinnamate sold under the trade name Neo Heliopan E 1000® by Symrise,
DEA methoxycinnamate,
Diisopropyl methylcinnamate,
Glyceryl Ethylhexanoate Dimethoxycinnamate.

Para-Aminobenzoic Compounds:
PABA,
Ethyl PABA,
Ethyl dihydroxypropyl PABA,
Ethylhexyl dimethyl PABA, sold in particular under the name Escalol 507® by ISP, Glyceryl PABA,
PEG-25 PABA, sold under the name Uvinul P 25® by BASF.

Salicylic Compounds:
Homosalate, sold under the name Eusolex HMS® by Rona/EM Industries,
Ethylhexyl salicylate, sold under the name Neo Heliopan OS® by Symrise,
Dipropylene glycol salicylate, sold under the name Dipsal® by Scher,
TEA salicylate, sold under the name Neo Heliopan TS® by Symrise.

β,β-Diphenylacrylate Compounds:
Octocrylene, sold in particular under the trade name Uvinul N 539® by BASF, Etocrylene, sold in particular under the trade name Uvinul N 35® by BASF.

Benzophenone Compounds:
Benzophenone-1 sold under the trade name Uvinul 400® by BASF,
Benzophenone-2, sold under the trade name Uvinul D 50® by BASF,
Benzophenone-3 or Oxybenzone, sold under the trade name Uvinul M 40® by BASF,
Benzophenone-4, sold under the trade name Uvinul MS 40® by BASF, Benzophenone-5,
Benzophenone-6, sold under the trade name Helisorb 11® by Norquay,
Benzophenone-8, sold under the trade name Spectra-Sorb UV-24® by American Cyanamid,
Benzophenone-9, sold under the trade name Uvinul DS 49® by BASF, Benzophenone-12,
n-Hexyl 2-(4-diethylamino-2-hydroxybenzoyl)benzoate, sold under the trade name Uvinul A Plus® or, as a mixture with octyl methoxycinnamate, under the trade name Uvinul A Plus B® by the company BASF,
1,1'-(1,4-Piperazinediyl)bis[1-[2-[4-(diethylamino)-2-hydroxybenzoyl]phenyl]methanone] (CAS 919803-06-8), as described in patent application WO 2007/071 584; this compound advantageously being used in micronized form (mean size of 0.02 to 2 μm), which may be obtained, for example, according to the micronization process described in patent applications GB-A-2 303 549 and EP-A-893 119, and in particular in the form of an aqueous dispersion.

Benzylidenecamphor Compounds:
3-Benzylidenecamphor, manufactured under the name Mexoryl SD® by Chimex,
4-Methylbenzylidenecamphor, sold under the name Eusolex 6300® by Merck,
Benzylidenecamphorsulfonic acid, manufactured under the name Mexoryl SL® by Chimex,
Camphor benzalkonium methosulfate, manufactured under the name Mexoryl SO® by Chimex,
Terephthalylidenedicamphorsulfonic acid, manufactured under the name Mexoryl SX® by Chimex,
Polyacrylamidomethylbenzylidenecamphor, manufactured under the name Mexoryl SW® by Chimex.

Phenylbenzimidazole Compounds:
Phenylbenzimidazolesulfonic acid, sold in particular under the trade name Eusolex 232® by Merck.

Bisbenzoazolyl Compounds:
Disodium phenyl dibenzimidazole tetrasulfonate sold under the trade name Neo Heliopan AP® by Haarmann and Reimer.

Phenylbenzotriazole Compounds:
Drometrizole trisiloxane, sold under the name Silatrizole® by Rhodia Chimie.

Methylenebis(Hydroxyphenylbenzotriazole) Compounds:
Methylene bis-benzotriazolyl tetramethylbutylphenol in particular in solid form, such as the product sold under the trade name MIXXIM BB/100® by Fairmount Chemical or in the form of an aqueous dispersion of micronized particles having a mean particle size which ranges from 0.01 to 5 μm and more preferentially from 0.01 to 2 μm and more particularly from 0.020 to 2 μm, with at least one alkylpolyglycoside surfactant of structure: $C_nH_{2n+1}(C_6H_{10}O_5)_xH$ in which n is an integer from 8 to 16 and x is the average degree of polymerization of the $(C_6H_{10}O_5)$ unit and ranges from 1.4 to 1.6, as described in patent GB-A-2 303 549, in particular sold under the trade name Tinosorb M® by BASF or in the form of an aqueous dispersion of micronized particles having a mean particle size which ranges from 0.02 to 2 μm and more preferentially from 0.01 to 1.5 μm and more particularly from 0.02 to 1 μm in the presence of at least one mono-($C_8$-$C_{20}$)alkyl ester of polyglycerol having a degree of glycerol polymerization of at least 5, such as the aqueous dispersions described in application WO 2009/063392.

Triazine Compounds:
Bis-ethylhexyloxyphenol methoxyphenyl triazine, sold under the trade name Tinosorb S® by BASF,
Ethylhexyltriazone sold in particular under the trade name Uvinul T 1500 by BASF,
Diethylhexyl butamido triazine, sold under the trade name Uvasorb HEB® by Sigma 3V,
2,4,6-tris(dineopentyl 4'-aminobenzalmalonate)-s-triazine,
2,4,6-tris(diisobutyl 4'-aminobenzalmalonate)-s-triazine,
2,4-bis(n-butyl 4'-aminobenzoate)-6-(aminopropyltrisiloxane)-s-triazine,
2,4-bis(dineopentyl 4'-aminobenzalmalonate)-6-(n-butyl 4'-aminobenzoate)-s-triazine,
symmetrical triazine screening agents substituted with naphthalenyl groups or polyphenyl groups described in U.S. Pat. No. 6,225,467, patent application WO 2004/085 412 (see compounds 6 and 9) or the document "Symmetrical Triazine Derivatives", IP.COM IPCOM000031257 Journal, INC West Henrietta, N.Y., US (20 Sep. 2004), in particular 2,4,6-tris(diphenyl)triazine and 2,4,6-tris(terphenyl)triazine, which is also mentioned in patent applications WO 06/035 000, WO 06/034 982, WO 06/034 991, WO 06/035 007, WO 2006/034 992 and WO 2006/034 985, these compounds advantageously being used in micronized form (mean particle size of 0.02 to 3 μm), which may be obtained, for example, according to the micronization process described in patent applications GB-A-2 303 549 and EP-A-893 119, and in particular in aqueous dispersion form,
Silicone triazines substituted with two aminobenzoate groups, as described in patent EP 0 841 341, in particular 2,4-bis(n-butyl 4'-aminobenzalmalonate)-6-[(3-{1,3,3,3-tetramethyl-1-[(trimethylsilyl)oxy]disiloxanyl}propyl)amino]-s-triazine.

Anthranilic Compounds:
Menthyl anthranilate sold under the trade name Neo Heliopan MA® by Symrise.

Imidazo Line Compounds:
Ethylhexyl dimethoxybenzylidene dioxoimidazo line propionate.

Benzalmalonate Compounds:
Polyorganosiloxane comprising benzalmalonate functions, such as Polysilicone-15, sold under the trade name Parsol SLX® by Hoffmann-LaRoche.

4,4-Diarylbutadiene Compounds:
1,1-Dicarboxy(2,2'-dimethylpropyl)-4,4-diphenylbutadiene.

Benzoxazole Compounds:
2,4-Bis[5-(1,1-dimethylpropyl)benzoxazol-2-yl(4-phenyl)imino]-6-(2-ethylhexyl)imino-1,3,5-triazine, sold under the name Uvasorb K2A® by Sigma 3V.

The preferential organic screening agents are chosen from:
Ethylhexyl methoxycinnamate
Ethylhexyl salicylate,
Homosalate,
Octocrylene,
Phenylbenzimidazolesulfonic acid,
Benzophenone-3,
Benzophenone-4,
Benzophenone-5,
n-Hexyl 2-(4-diethylamino-2-hydroxybenzoyl)benzoate,
4-Methylbenzylidene camphor,
Terephthalylidenedicamphorsulfonic acid,
Disodium phenyl dibenzimidazole tetrasulfonate,
Methylenebis(benzotriazolyl)tetramethylbutylphenol,
Bis-ethylhexyloxyphenol methoxyphenyl triazine,
Ethylhexyl triazone
Diethylhexyl butamido triazone,
2,4,6-Tris(dineopentyl 4'-aminobenzalmalonate)-s-triazine,
2,4,6-Tris(diisobutyl 4'-aminobenzalmalonate)-s-triazine,
2,4-Bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
2,4-Bis(n-butyl 4'-aminobenzalmalonate)-6-[(3-{1,3,3,3-tetramethyl-1-[(trimethylsilyl)oxy]disiloxanyl}propyl)amino]-s-triazine,
2,4,6-Tris(diphenyl)triazine,
2,4,6-Tris(terphenyl)triazine,
Drometrizole trisiloxane,
Polysilicone-15,
1,1-Dicarboxy(2,2'-dimethylpropyl)-4,4-diphenylbutadiene;
2,4-Bis[5-(1-dimethylpropyl)benzoxazol-2-yl-(4-phenyl)imino]-6-(2-ethylhexyl)imino-1,3,5-triazine,
and mixtures thereof.

The particularly preferred organic screening agents are chosen from:
Ethylhexyl salicylate,
Homosalate,
Octocrylene,
n-Hexyl 2-(4-diethylamino-2-hydroxybenzoyl)benzoate,
Terephthalylidenedicamphorsulfonic acid,
Bis-ethylhexyloxyphenol methoxyphenyl triazine,
Ethylhexyl triazone
Diethylhexyl butamido triazone,
2,4-Bis(n-butyl 4'-aminobenzalmalonate)-6-[(3-{1,3,3,3-tetramethyl-1-[(trimethylsilyl)oxy]disiloxanyl}propyl)amino]-s-triazine,
Drometrizole trisiloxane,
and mixtures thereof.

The inorganic UV-screening agents used in accordance with the present invention are metal oxide pigments. More preferentially, the inorganic UV-screening agents of the invention are metal oxide particles with a mean elementary particle size of less than or equal to 0.5 μm, more preferentially between 0.005 and 0.5 μm, even more preferentially between 0.01 and 0.2 μm, better still between 0.01 and 0.1 μm and more particularly between 0.015 and 0.05 μm.

They may be chosen in particular from titanium oxide, zinc oxide, iron oxide, zirconium oxide and cerium oxide, or mixtures thereof.

Such coated or uncoated metal oxide pigments are described in particular in patent application EP-A-0 518 773. Commercial pigments that may be mentioned include the products sold by the companies Sachtleben Pigments, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides that have been coated:

- with silica, such as the product Sunveil® from the company Ikeda,
- with silica and iron oxide, such as the product Sunveil F® from the company Ikeda,
- with silica and alumina, such as the products Microtitanium Dioxide MT 500 SA® and Microtitanium Dioxide MT 100 SA from the company Tayca and Tioveil from the company Tioxide,
- with alumina, such as the products Tipaque TTO-55 (B)® and Tipaque TTO-55 (A)® from the company Ishihara and UVT 14/4 from the company Sachtleben Pigments,
- with alumina and aluminium stearate, such as the products Microtitanium Dioxide MT 100 T®, MT 100 TX®, MT 100 Z® and MT-01® from the company Tayca, the products Solaveil CT-10 W® and Solaveil CT 100® from the company Croda and the product Eusolex T-AVO® from the company Merck,
- with silica, alumina and alginic acid, such as the product MT-100 AQ® from the company Tayca,
- with alumina and aluminium laurate, such as the product Microtitanium Dioxide MT 100 S® from the company Tayca,
- with iron oxide and iron stearate, such as the product Microtitanium Dioxide MT 100 F® from the company Tayca,
- with zinc oxide and zinc stearate, such as the product BR 351® from the company Tayca,
- with silica and alumina and treated with a silicone, such as the products Microtitanium Dioxide MT 600 SAS®, Microtitanium Dioxide MT 500 SAS® or Microtitanium Dioxide MT 100 SAS® from the company Tayca,
- with silica, alumina and aluminium stearate and treated with a silicone, such as the product STT-30-DS® from the company Titan Kogyo,
- with silica and treated with a silicone, such as the product UV-Titan X 195® from the company Sachtleben Pigments,
- with alumina and treated with a silicone, such as the products Tipaque TTO-55 (S)® from the company Ishihara or UV Titan M 262® from the company Sachtleben Pigments,
- with triethanolamine, such as the product STT-65-S from the company Titan Kogyo,
- with stearic acid, such as the product Tipaque TTO-55 (C)® from the company Ishihara,
- with sodium hexametaphosphate, such as the product Microtitanium Dioxide MT 150 W® from the company Tayca,
- $TiO_2$ treated with octyltrimethylsilane, sold under the trade name T 805® by the company Degussa Silices,
- $TiO_2$ treated with a polydimethylsiloxane, sold under the trade name 70250 Cardre UF $TiO_2SI3$® by the company Cardre,
- anatase/rutile $TiO_2$ treated with a polydimethylhydrogenosiloxane, sold under the trade name Micro Titanium Dioxide USP Grade Hydrophobic® by the company Color Techniques.
- $TiO_2$ coated with triethylhexanoin, with aluminium stearate and with alumina sold under the trade name Solaveil CT-200-LQ-(WD) by Croda,
- $TiO_2$ coated with aluminium stearate, with alumina and with silicone sold under the trade name Solaveil CT-12W-LQ-(WD) by Croda,
- $TiO_2$ coated with lauroyl lysine sold by Daito Kasei Kogyo under the name LL 5 Titanium Dioxyde CR 50,
- $TiO_2$ coated with $C_9$-$C_{15}$ fluoroalcohol phosphate and with aluminium hydroxide sold by Daito Kasei Kogyo under the name PFX-5 $TiO_2$ CR-50.

Mention may also be made of $TiO_2$ pigments doped with at least one transition metal such as iron, zinc or manganese and more particularly manganese. Preferably, said doped pigments are in the form of an oily dispersion. The oil present in the oily dispersion is preferably chosen from triglycerides including those of capric/caprylic acids. The oily dispersion of titanium oxide particles may also comprise one or more dispersants, for instance a sorbitan ester, for instance sorbitan isostearate, or a polyoxyalkylenated fatty acid ester of glycerol, for instance TRI-PPG-3 myristyl ether citrate and polyglyceryl-3 polyricinoleate. Preferably, the oily dispersion of titanium oxide particles comprises at least one dispersant chosen from polyoxyalkylenated fatty acid esters of glycerol. Mention may be made more particularly of the oily dispersion of $TiO_2$ particles doped with manganese in capric/caprylic acid triglyceride in the presence of TRI-PPG-3 myristyl ether citrate and polyglyceryl-3 polyricinoleate and sorbitan isostearate having the INCI name: titanium dioxide (and) TRI-PPG-3 myristyl ether citrate (and) polyglyceryl-3 ricinoleate (and) sorbitan isostearate, for instance the product sold under the trade name Optisol TD50® by the company Croda.

The uncoated titanium oxide pigments are sold, for example, by the company Tayca under the trade names Microtitanium Dioxide MT 500 B or Microtitanium Dioxide MT 600 B®, by the company Degussa under the name P 25, by the company Wackher under the name Transparent titanium oxide PW®, by the company Miyoshi Kasei under the name UFTR®, by the company Tomen under the name ITS® and by the company Tioxide under the name Tioveil AQ.

The uncoated zinc oxide pigments are, for example:
- those sold under the name Z-Cote by Sunsmart;
- those sold under the name Nanox® by the company Elementis;
- those sold under the name Nanogard WCD 2025® by the company Nanophase Technologies.

The coated zinc oxide pigments are, for example:
- those sold under the name Zinc Oxide CS-5® by the company Toshibi (ZnO coated with polymethylhydrogenosiloxane);
- those sold under the name Nanogard Zinc Oxide FN® by the company Nanophase Technologies (as a 40% dispersion in Finsolv TN®, $C_{12}$-$C_{15}$ alkyl benzoate);
- those sold under the name Daitopersion Zn-30® and Daitopersion Zn-50® by the company Daito (dispersions in cyclopolymethylsiloxane/oxyethylenated polydimethylsiloxane, containing 30% or 50% of zinc oxides coated with silica and polymethylhydrogenosiloxane);
- those sold under the name NFD Ultrafine ZnO® by the company Daikin (ZnO coated with perfluoroalkyl phosphate and copolymer based on perfluoroalkylethyl as a dispersion in cyclopentasiloxane);
- those sold under the name SPD-Z1® by the company Shin-Etsu (ZnO coated with silicone-grafted acrylic polymer, dispersed in cyclodimethylsiloxane);

those sold under the name Escalol Z100® by the company ISP (alumina-treated ZnO dispersed in the ethylhexyl methoxycinnamate/PVP-hexadecene copolymer/methicone mixture);

those sold under the name Fuji ZnO-SMS-100 by the company Fuji Pigment (ZnO coated with silica and polymethylsilsesquioxane);

those sold under the name Nanox Gel TN® by the company Elementis (ZnO dispersed at a concentration of 55% in $C_{12}$-$C_{15}$ alkyl benzoate with hydroxystearic acid polycondensate).

The uncoated cerium oxide pigments may be, for example, those sold under the name Colloidal Cerium Oxide® by the company Rhone-Poulenc.

The uncoated iron oxide pigments are sold, for example, by the company Arnaud under the names Nanogard WCD 2002® (FE 45B®), Nanogard Iron FE 45 BL AQ, Nanogard FE 45R AQ® and Nanogard WCD 2006® (FE 45R®) or by the company Mitsubishi under the name TY-220®.

The coated iron oxide pigments are sold, for example, by the company Arnaud under the names Nanogard WCD 2008 (FE 45B FN)®, Nanogard WCD 2009® (FE 45B 556®), Nanogard FE 45 BL 345® and Nanogard FE 45 BL® or by the company BASF under the name Transparent Iron Oxide®.

Mention may also be made of mixtures of metal oxides, especially of titanium dioxide and of cerium dioxide, including the equal-weight mixture of titanium dioxide and cerium dioxide coated with silica, sold by the company Ikeda under the name Sunveil A®, and also the mixture of titanium dioxide and zinc dioxide coated with alumina, silica and silicone, such as the product M 261® sold by the company Sachtleben Pigments, or coated with alumina, silica and glycerol, such as the product M 211® sold by the company Sachtleben Pigments.

According to the invention, coated or uncoated titanium oxide pigments are particularly preferred.

According to one preferred embodiment of the invention, the composition also comprises one or more additional UV-screening agents chosen from hydrophilic, lipophilic or insoluble organic UV-screening agents and/or one or more mineral pigments; more preferentially chosen, alone or as a mixture, from anthranilates; salicylic derivatives; benzylidenecamphor derivatives; benzophenone derivatives; β,β-diphenylacrylate compounds different from ethylhexyl methoxycrylene derivatives; triazine derivatives such as derivatives of bisresorcinyl triazine type; benzotriazole derivatives; benzalmalonate derivatives; benzimidazole derivatives; imidazo lines; bisbenzoazolyl derivatives; p-aminobenzoic acid (PABA) derivatives; methylenebis(hydroxyphenyl benzotriazole) derivatives; benzoxazole derivatives; screening polymers and screening silicones; α-alkylstyrene-based dimers; 4,4-diarylbutadienes; and/or treated or untreated metal oxide pigments or nanopigments, such as titanium oxides, zinc oxides, iron oxides, zirconium oxides, cerium oxides and mixtures thereof, preferably chosen, alone or as a mixture, from titanium oxides.

According to a very preferred embodiment of the invention, the composition according to the present invention also comprises one or more additional UV-screening agents chosen, alone or as a mixture, from the following UV-screening agents: ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, 4-methylbenzylidenecamphor, terephthalylidenedicamphorsulfonic acid, disodium phenyldibenzimidazole tetrasulfonate, methylenebisbenzotriazolyl tetramethylbutylphenol, ethylhexyl triazone, diethylhexyl butamido triazone, drometrizole trisiloxane, polysilicone-15, 1,1-dicarboxy(2,2'-dimethylpropyl)-4,4-diphenylbutadiene, 2,4-bis[5,1(dimethylpropyl)benzoxazol-2-yl(4-phenyl)imino]-6-(2-ethylhexyl)imino-1,3,5-triazine, and mixtures thereof.

The amount of additional UV-screening agent(s) present in the composition according to the invention may range from 0.1% to 50% by weight, relative to the total weight of the composition. It preferably ranges from 0.2% to 30% by weight, more preferentially from 0.5% to 25% by weight and better still ranges from 1% to 15% by weight, relative to the total weight of the composition.

Surfactants

The composition according to the present invention may optionally also comprise one or more surfactants.

The surfactants according to the invention are preferably selected from anionic surfactants, non-ionic surfactants and/or gemini surfactants, and mixtures thereof.

The anionic surfactants that may be present in the composition according to the invention may be chosen especially from anionic derivatives of proteins of plant origin or of silk proteins, phosphates and alkyl phosphates, carboxylic acids and carboxylates, sulfosuccinates, amino acid derivatives, alkyl sulfates, alkyl ether sulfates, sulfonates, isethionates, taurates, alkyl sulfoacetates, polypeptides, anionic derivatives of alkyl polyglucoside, soaps (fatty acid salts), and mixtures thereof.

a) Anionic derivatives of proteins of plant origin are protein hydrolysates bearing a hydrophobic group, it being possible for said hydrophobic group to be naturally present in the protein or to be added by reaction of the protein and/or of the protein hydrolysate with a hydrophobic compound. The proteins are of plant origin or are derived from silk, and the hydrophobic group may in particular be a fatty chain, for example an alkyl chain comprising from 10 to 22 carbon atoms. As anionic derivatives of proteins of plant origin, mention may more particularly be made of apple, wheat, soybean or oat protein hydrolysates comprising an alkyl chain having from 10 to 22 carbon atoms, and salts thereof. The alkyl chain may especially be a lauryl chain and the salt may be a sodium, potassium and/or ammonium salt.

Thus, as protein hydrolysates bearing a hydrophobic group, mention may be made, for example, of salts of protein hydrolysates where the protein is a silk protein modified with lauric acid, such as the product sold under the name Kawa Silk by Kawaken; salts of protein hydrolysates where the protein is a wheat protein modified with lauric acid, such as the potassium salt sold under the name Aminofoam W OR by Croda (CTFA name: potassium lauroyl wheat amino acids) and the sodium salt sold under the name Proteol LW 30 by the company SEPPIC (CTFA name: sodium lauroyl wheat amino acids); salts of protein hydrolysates where the protein is an oat protein comprising an alkyl chain containing from 10 to 22 carbon atoms and more especially salts of protein hydrolysates where the protein is an oat protein modified with lauric acid, such as the sodium salt sold under the name Proteol OAT (30% aqueous solution) by the company SEPPIC (CTFA name: sodium lauroyl oat amino acids); or salts of apple protein hydrolysates comprising an alkyl chain containing from 10 to 22 carbon atoms, such as the sodium salt sold under the name Proteol APL (30% aqueous glycol solution) by the company SEPPIC (CTFA name: Sodium Cocoyl Apple amino acids). Mention may also be made of the mixture of lauroyl amino acids (aspartic acid, glutamic acid, glycine, alanine) neutralized with sodium N-methylglycinate sold under the name Proteol SAV 50 S by the company SEPPIC (CTFA name: Sodium Cocoyl amino acids).

b) Examples of phosphates and alkyl phosphates that may be mentioned include monoalkyl phosphates and dialkyl phosphates, such as the lauryl monophosphate sold under the name MAP 20® by the company Kao Chemicals, the potassium salt of dodecylphosphoric acid, mixture of monoester and diester (predominantly diester) sold under the name Crafol AP-31® by the company Cognis, the mixture of octylphosphoric acid monoester and diester sold under the name Crafol AP-20® by the company Cognis, the mixture of ethoxylated (7 mol of EO) phosphoric acid monoester and diester of 2-butyloctanol, sold under the name Isofol 12 7 EO-Phosphate Ester® by the company Condea, the potassium or triethanolamine salt of mono($C_{12}$-$C_{13}$)alkyl phosphate sold under the references Arlatone MAP 230K-40® and Arlatone MAP 230T-60® by the company Uniqema, the potassium lauryl phosphate sold under the name Dermalcare MAP XC-99/09® by the company Rhodia Chimie, and the potassium cetyl phosphate sold under the name Arlatone MAP 160K by the company Uniqema.

c) As carboxylic acids and carboxylates, mention may for example be made of amide ether carboxylates (AECs), such as sodium laurylamide ether carboxylate (3 EO), sold under the name Akpyo Foam 30® by the company Kao Chemicals, polyoxyethylenated carboxylic acid salts, such as oxyethylenated (6 EO) sodium lauryl ether carboxylate ($C_{12}$-14-16 65/25/10) sold under the name Akpyo Soft 45 NV® by the company Kao Chemicals, polyoxyethylenated and carboxymethylated fatty acids of olive oil origin, sold under the name Olivem 400® by the company Biologia E Tecnologia, oxyethylenated (6 EO) sodium tridecyl ether carboxylate sold under the name Nikkol ECTD-6NEX® by the company Nikkol, fatty acids having a $C_6$ to $C_{22}$ alkyl chain, such as stearic acid, and fatty acid salts (soaps) having a $C_6$ to $C_{22}$ alkyl chain, neutralized with an organic or mineral base such as potassium hydroxide, sodium hydroxide, triethanolamine, N-methyl glucamine, lysine and arginine.

d) Amino acid derivatives that may especially be mentioned include alkaline salts of amino acids, such as:

sarcosinates, for instance sodium cocoyl sarcosinate, the sodium lauroyl sarcosinate sold under the name Sarkosyl NL 97® by the company Ciba or sold under the name Oramix L 30® by the company SEPPIC, sodium myristoyl sarcosinate sold under the name Nikkol Sarcosinate MN® by the company Nikkol, and sodium palmitoyl sarcosinate sold under the name Nikkol Sarcosinate PN® by the company Nikkol;

alaninates, for instance sodium N-lauroyl N-methyl amidopropionate sold under the name Sodium Nikkol Alaninate LN 30® by the company Nikkol, or sold under the name Alanone ALE® by the company Kawaken, and triethanolamine N-lauroyl N-methyl alanine sold under the name Alanone Alta® by the company Kawaken;

glutamates, for instance triethanolamine monococoyl glutamate sold under the name Acylglutamate CT-12® by the company Ajinomoto, triethanolamine lauroyl glutamate sold under the name Acylglutamate LT-12® by the company Ajinomoto, aspartates, for instance the mixture of triethanolamine N-lauroyl aspartate/triethanolamine N-myristoyl aspartate sold under the name Asparack® by the company Mitsubishi;

glycine derivatives (glycinates), for instance the sodium N-cocoyl glycinate sold under the names Amilite GCS-12® and Amilite GCK 12 by the company Ajinomoto;

citrates, such as the oxyethylenated (9 mol) citric monoester of cocoyl alcohols sold under the name Witconol EC 1129 by the company Goldschmidt, and galacturonates such as sodium dodecyl D-galactoside uronate sold by the company Soliance.

e) Examples of sulfosuccinates that may be mentioned include the oxyethylenated (3 EO) lauryl alcohol monosulfosuccinate (70/30 $C_{12}$/$C_{14}$) sold under the names Setacin 103 Special® and Rewopol SB-FA 30 K 4® by the company Witco, the disodium salt of a hemisulfosuccinate of $C_{12}$-$C_{14}$ alcohols, sold under the name Setacin F Special Paste® by the company Zschimmer Schwarz, the oxyethylenated (2 EO) disodium oleamidosulfosuccinate sold under the name Standapol SH 135® by the company Cognis, the oxyethylenated (5 EO) laurylamide monosulfosuccinate sold under the name Lebon A-5000® by the company Sanyo, the oxyethylenated (10 EO) disodium salt of lauryl citrate monosulfosuccinate sold under the name Rewopol SB CS 50® by the company Witco, and the ricinoleic monoethanolamide monosulfosuccinate sold under the name Rewoderm S 1333® by the company Witco. Polydimethylsiloxane sulfosuccinates may also be used, such as the disodium PEG-12 dimethicone sulfosuccinate sold under the name Mackanate-$DC_{30}$ by the company MacIntyre.

f) Examples of alkyl sulfates that may be mentioned include triethanolamine lauryl sulfate (CTFA name: TEA lauryl sulfate), such as the product sold by Huntsman under the name Empicol TL40 FL or the product sold by Cognis under the name Texapon T42, which products are at 40% in aqueous solution. Mention may also be made of ammonium lauryl sulfate (CTFA name: ammonium lauryl sulfate), such as the product sold by Huntsman under the name Empicol AL 30FL, which is at 30% in aqueous solution.

g) Examples of alkyl ether sulfates that may be mentioned include sodium lauryl ether sulfate (CTFA name: sodium laureth sulfate), such as the product sold under the names Texapon N40 and Texapon AOS 225 UP by the company Cognis, or ammonium lauryl ether sulfate (CTFA name: ammonium laureth sulfate), such as the product sold under the name Standapol EA-2 by the company Cognis.

h) Examples of sulfonates that may be mentioned include α-olefinsulfonates, such as the sodium α-olefinsulfonate ($C_{14}$-$C_{16}$), sold under the name Bio-Terge AS-40® by the company Stepan, sold under the names Witconate AOS Protege® and Sulframine AOS PH 12® by the company Witco or sold under the name Bio-Terge AS-40 CG® by the company Stepan, secondary sodium olefinsulfonate, sold under the name Hostapur SAS 30® by the company Clariant; or linear alkylarylsulfonates, such as sodium xylenesulfonate, sold under the names Manrosol SXS30®, Manrosol SXS40® and Manrosol SXS93® by the company Manro.

i) Isethionates that may be mentioned include ($C_8$-$C_{18}$) acylisethionates, for instance sodium cocoyl isethionate, such as the product sold under the name Jordapon CI P® by the company Jordan.

j) Taurates that may be mentioned include the salts (in particular sodium salt) of palm kernel oil methyltaurate sold under the name Hostapon CT Pate® by the company Clariant; N—($C_8$-$C_{18}$)acyl N-methyltaurates, for instance the sodium N-cocoyl N-methyltaurate sold under the name Hostapon LT-SF® by the company Clariant or sold under the name Nikkol CMT-30-T® by the company Nikkol, and the sodium palmitoyl methyltaurate sold under the name Nikkol PMT® by the company Nikkol.

k) The anionic derivatives of ($C_8$-$C_{18}$)alkyl polyglucosides may especially be citrates, tartrates, sulfosuccinates, carbonates and ethers of glycerol obtained from alkyl polyglucosides. Mention may be made, for example, of the sodium salt of cocoylpolyglucoside (1,4) tartaric ester, sold under the name Eucarol AGE-ET® by Cesalpinia, the disodium salt of cocoylpolyglucoside (1,4) sulfosuccinic ester, sold under the name Essai 512 MP® by Seppic, or the sodium salt of cocoylpolyglucoside (1,4) citric ester, sold under the name Eucarol AGE-EC® by Cesalpinia.

l) The soaps are obtained from a fatty acid which is partially or completely saponified (neutralized) with a basic agent. These are alkali metal or alkaline-earth metal soaps or soaps of organic bases. Use may be made, as fatty acids, of saturated, linear or branched fatty acids comprising from 8 to 30 carbon atoms and preferably comprising from 8 to 22 carbon atoms. This fatty acid may be chosen in particular from palmitic acid, stearic acid, myristic acid and lauric acid, and mixtures thereof.

Examples of basic agents that may be used include alkali metal hydroxides (sodium hydroxide and potassium hydroxide), alkaline-earth metal hydroxides (for example magnesium hydroxide), ammonium hydroxide or else organic bases, such as triethanolamine, N-methylglucamine, lysine and arginine.

The soaps may especially be fatty acid alkali metal salts, the basic agent being an alkali metal hydroxide and preferably potassium hydroxide (KOH).

The amount of basic agent must be sufficient for the fatty acid to be at least partially neutralized.

Preferably, the anionic surfactant(s) are chosen from alkyl sulfates, alkyl ether sulfates such as sodium lauryl ether sulfate, phosphates, alkylphosphates such as potassium cetylphosphate, amino acid derivatives, in particular sarcosine derivatives (sarcosinates), such as sodium cocoyl sarcosinate, soaps such as sodium stearate, carboxylic acids such as stearic acid, and mixtures thereof.

Preferentially, the anionic surfactant(s) are chosen from phosphates, alkylphosphates such as potassium cetylphosphate, sarcosine derivatives (sarcosinates), such as sodium cocoyl sarcosinate, soaps such as sodium stearate, carboxylic acids such as stearic acid, and mixtures thereof.

The non-ionic surfactants that may be present in the composition of the invention can be chosen in particular from alkyl polyglucosides (APGs), oxyalkylenated glycerol esters, oxyalkylenated fatty acid esters of sorbitan, polyoxyalkylenated (in particular polyoxyethylenated and/or polyoxypropylenated) fatty acid esters optionally in combination with a fatty acid ester of glycerol, such as the PEG-100 stearate/glyceryl stearate mixture sold for example by the company ICI under the name Arlacel 165, oxyalkylenated sugar esters, and mixtures thereof.

Use is preferably made, as alkyl polyglucosides, of those containing an alkyl group comprising from 6 to 30 carbon atoms and preferably from 8 to 16 carbon atoms and containing a glucoside group preferably comprising from 1.2 to 3 glucoside units. The alkylpolyglucosides may be chosen, for example, from decylglucoside (alkyl-$C_9/C_{11}$-polyglucoside (1.4)), for instance the product sold under the name Mydol 100 by the company Kao Chemicals or the product sold under the name Plantacare 2000 UP® by the company Cognis; caprylyl/capryl glucoside, for instance the product sold under the name Plantacare KE 3711® by the company Cognis; laurylglucoside, for instance the product sold under the name Plantacare 1200 UP® by the company Cognis; cocoyl glucoside, for instance the product sold under the name Plantacare 818 UP® by the company Cognis; caprylylglucoside, for instance the product sold under the name Plantacare 810 UP® by the company Cognis; and mixtures thereof.

The oxyalkylenated glycerol esters are especially polyoxyethylenated derivatives of esters of glycerol and of a fatty acid and of their hydrogenated derivatives. These oxyalkylenated glycerol esters can be chosen, for example, from glyceryl esters of fatty acids which are hydrogenated and oxyethylenated, such as PEG-200 hydrogenated glyceryl palmate, sold under the name Rewoderm LI-S 80 by the company Goldschmidt; oxyethylenated glyceryl cocoates, such as PEG-7 glyceryl cocoate, sold under the name Tegosoft GC by the company Goldschmidt, and PEG-30 glyceryl cocoate, sold under the name Rewoderm LI-63 by the company Goldschmidt; oxyethylenated glyceryl stearates; and mixtures thereof.

The oxyalkylenated sugar esters are especially polyethylene glycol ethers of fatty acid and sugar esters. These oxyalkylenated sugar esters may be chosen, for example, from oxyethylenated glucose esters, such as PEG-120 methyl glucose dioleate, sold under the name Glucamate DOE 120 by the company Amerchol.

Preferably, the non-ionic surfactant(s) are chosen, alone or as a mixture, from oxyalkylenated glycerol esters and polyoxyalkylenated fatty acid esters optionally in combination with a fatty acid ester of glycerol.

Preferentially, the non-ionic surfactant(s) are chosen from PEG-200 hydrogenated glyceryl palmate, PEG-7 glyceryl cocoate and PEG-30 glyceryl cocoate, the PEG-100 stearate/glyceryl stearate mixture; and mixtures thereof.

In the context of the present invention, the term "gemini surfactant" is intended to mean a dimer surfactant comprising two surfactant units, each constituted of a hydrophilic head and a hydrophobic tail and linked to one another, at the hydrophilic heads, by a spacer group.

The gemini surfactants that can be used in the present invention are in particular assembled in German patent application DE 199 43 681, namely the compounds of formula (XI), described in WO 96/14926:

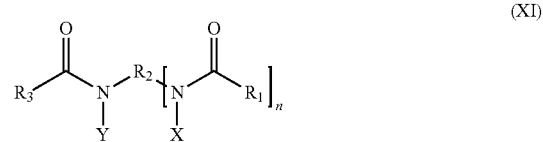

(XI)

in which:
$R_1$ and $R_3$ denote, independently of each other, an alkyl radical containing from 1 to 25 carbon atoms;
$R_2$ denotes a spacer group constituted of a linear or branched alkylene chain containing from 1 to 12 carbon atoms;
X denotes a —$(C_2H_4O)_a$—$(C_3H_6O)_b$Z group
Y denotes a —$(C_2H_4O)_c$—$(C_3H_6O)_d$Z group
Z denotes a hydrogen atom or a radical —$CH_2$—COOM, —$SO_3M$, —P(I)(OM)$_2$, —$C_2H_4$—$SO_3M$, —$C_3H_6$—$SO_3M$ or —$CH_2(CHOH)_4CH_2H$, where M and M' represent a hydrogen atom or an alkali metal or alkaline-earth metal ion or ammonium or alkanolammonium ion,
a and c, independently of one another, range from 0 to 15,
b and d, independently of one another, range from 0 to 10, and
the sum of a+b+c+d ranges from 1 to 25; and
n ranges from 1 to 10.
Preferably, b and d are equal to 0.

$R_1$ and $R_3$ denote, independently of each other, preferably an alkyl radical containing from 5 to 21 and more particularly from 7 to 19 carbon atoms.

The gemini surfactant(s) are preferably such that each of the groups $R_1$—CO— and $R_3$—CO— comprises from 8 to 20 carbon atoms, and preferably denotes a coconut fatty acid residue (mainly comprising lauric acid and myristic acid).

In addition, the gemini surfactant(s) are preferably such that the sum of a, b, c and d has an average value ranging from 10 to 20 and is preferably from 12 to 18 and more particularly equal to 15.

A preferred group for Z is the group —$SO_3M$, where M is preferably an alkali metal ion, such as a sodium ion.

The spacer group $R_2$ is advantageously constituted of a linear $C_1$-$C_3$ alkylene chain, and preferably an ethylene (—$CH_2CH_2$—) chain.

Finally, n is advantageously equal to 1.

A gemini surfactant is in particular the one identified by the INCI name: Disodium Ethylene Dicocamide PEG-15 Disulfate, having the following structure:

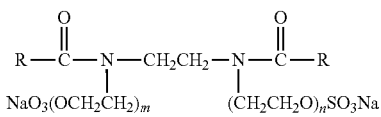

in which R represents a coconut oil fatty acid and m+n has an average value of 15.

Preferably, the gemini surfactant(s) according to the invention are used as a mixture with other surfactants, and in particular as a mixture with (a) a glyceryl ester of a $C_6$-$C_{22}$ fatty acid (preferably $C_{14}$-$C_{20}$ such as a stearate), (b) a diester of a $C_6$-$C_{22}$ fatty acid (preferably $C_{14}$-$C_{20}$ such as a stearate) and of citric acid and of glycerol (in particular a diester of a $C_6$-$C_{22}$ fatty acid and of glyceryl monocitrate), and (c) a $C_{10}$-$C_{30}$ fatty alcohol (preferably behenyl alcohol).

The gemini surfactant(s) may be used, for example, as a mixture with other surfactants in the form of the products sold by the company Sasol under the name Ceralution®, and in particular the following products:

Ceralution® H: Behenyl Alcohol, Glyceryl Stearate, Glyceryl Stearate Citrate and disodium ethylene dicocoamide PEG-15 disulfate, Ceralution® F: Sodium Lauroyl Lactylate and disodium ethylene dicocamide PEG-15 disulfate.

Ceralution® C: Capric/Caprylic triglyceride, Ceteareth-25, disodium ethylene dicocamide PEG-15 disulfate, Sodium Lauroyl Lactylate, Behenyl Alcohol, Glyceryl Stearate, Glyceryl Stearate Citrate, (INCI names).

The gemini surfactant represents from 3 to 50% of the weight of these mixtures.

The gemini surfactant can be present in the composition according to the invention in a content of active material ranging from 0.05 to 10% by weight, preferably ranging from 0.1 to 5% by weight and better still ranging from 0.2 to 2% by weight, relative to the total weight of the composition.

According to one preferred embodiment of the invention, the composition according to the present invention also comprises one or more surfactants chosen from PEG-200 hydrogenated glyceryl palmate, PEG-7 glyceryl cocoate, PEG-30 glyceryl cocoate, the PEG-100 stearate/glyceryl stearate mixture, stearic acid, disodium ethylene dicocamide PEG-15 disulfate; and mixtures thereof.

The surfactant(s) can also be chosen from silicone surfactants, for instance dimethicone copolyols, such as the mixture of cyclomethicone and of dimethicone copolyol, sold under the name DC 5225 C® by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R® by the company Goldschmidt, and the mixture of cetyldimethicone copolyol, of polyglyceryl isostearate (4 mol) and of hexyl laurate, sold under the name Abil WE 09® by the company Goldschmidt. One or more coemulsifiers, which may be chosen advantageously from the group comprising polyol alkyl esters, may also be added thereto.

Mention may also be made of non-silicone emulsifying surfactants, in particular alkyl esters or ethers of a polyol. As alkyl esters of a polyol, mention may in particular be made of polyethylene glycol esters, for instance PEG-30 dipolyhydroxystearate, such as the product sold under the name Arlacel P135® by the company ICI.

Amphiphilic Polymers

The composition according to the present invention may optionally also comprise one or more amphiphilic polymers.

The amphiphilic polymer(s) used in the composition according to the invention can be polymers derived from 2-acrylamido-2-methylpropanesulfonic acid (AMPS) comprenant:

(a) from 80 mol % to 99 mol % of 2-acrylamido-2-methylpropanesulfonic acid (AMPS) units of formula (XII) below:

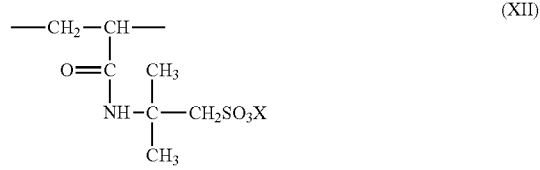

in which X is a proton, an alkali metal cation, an alkaline-earth metal cation or the ammonium ion; it being understood that when X represents an alkaline-earth metal cation, it shares two positive charges with two $SO_3^-$ groups; and (b) from 1 mol % to 20 mol % and preferably from 1 mol % to 15 mol % of units of formula (XIIbis) below:

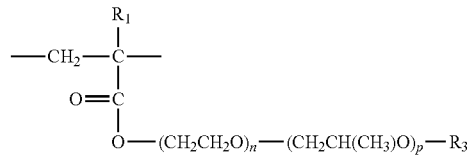

in which n and p, independently of each other, denote a number of moles and ranges from 0 to 30 and preferably from 1 to 20, with the proviso that n+p is less than or equal to 30, preferably less than 25 and better still less than 20; $R_1$ denotes a hydrogen atom or a linear or branched $C_1$-$C_6$ alkyl radical (preferably methyl) and $R_3$ denotes a linear or branched alkyl group comprising m carbon atoms, ranging from 6 to 30 and preferably from 10 to 25 carbon atoms.

The term "amphiphilic polymer" is intended to mean a polymer which comprises at least one hydrophilic portion (or block) and at least one hydrophobic portion (or block). This polymer is water-soluble or water-dispersible.

The amphiphilic polymers used in the composition of the invention are water-soluble or water-dispersible. The term "water-soluble or water-dispersible polymer" is intended to mean a polymer which, when introduced into water at a concentration equal to 1% by weight, gives a macroscopically homogeneous solution of which the light transmittance, at a wavelength equal to 500 nm, through a sample 1 cm thick, is at least 10%, which corresponds to an absorbance [abs=−log(transmittance)] of less than 1.5.

The amphiphilic polymers in accordance with the invention generally have a weight-average molar mass ranging from 50 000 to 10 000 000, more preferentially from 100 000 to 8 000 000 and even more preferentially from 200 000 to 3 000 000.

The polymers in accordance with the invention are preferentially partially or totally neutralized with a mineral base, for instance sodium hydroxide, potassium hydroxide or aqueous ammonia, or with an organic base such as monoethanolamine, diethanolamine, triethanolamine, aminomethylpropanediol, N-methylglucamine, or basic amino acids, for instance arginine and lysine, and mixtures thereof.

The polymers used according to the invention may be obtained according to the standard free-radical polymerization processes in the presence of one or more initiators such as, for example, azobisisobutyronitrile (AIBN), azobisdimethylvaleronitrile, 2,2-azobis[2-amidinopropane] hydrochloride (ABAH), organic peroxides such as dilauryl peroxide, benzoyl peroxide, tert-butyl hydroperoxide, etc., mineral peroxide compounds such as potassium persulfate or ammonium persulfate, or $H_2O_2$ optionally in the presence of reducing agents.

The polymers are obtained especially by free-radical polymerization in tert-butanol medium in which they precipitate. Using polymerization in tert-butanol, it is possible to obtain a size distribution of the polymer particles that is particularly favourable for its uses.

The polymerization reaction may be performed at a temperature of between 0 and 150° C., preferably between 20 and 100° C., either at atmospheric pressure or under reduced pressure. It may also be performed under inert atmosphere and preferably under nitrogen.

The amphiphilic polymers of AMPS used in the composition according to the invention are non-crosslinked.

As AMPS-based polymers that may be used in the composition according to the invention, mention may be made of the polymers prepared from 2-acrylamido-2-methylpropanesulfonic acid (AMPS) or a sodium or ammonium salt thereof, with an ester of (meth)acrylic acid and of an oxyethylenated $C_{10}$ to $C_{20}$ alcohol comprising from 6 to 25 oxyethylene groups.

Mention may be made in particular of the polymers prepared from 2-acrylamido-2-methylpropanesulfonic acid (AMPS), or a sodium or ammonium salt thereof, with an ester of (meth)acrylic acid and:
- of a $C_{10}$-$C_{18}$ alcohol oxyethylenated with 8 mol of ethylene oxide (Genapol C-080 from Clariant),
- of a $C_{11}$ oxo alcohol oxyethylenated with 8 mol of ethylene oxide (Genapol UD-080 from Clariant),
- of a $C_{11}$ oxo alcohol oxyethylenated with 7 mol of ethylene oxide (Genapol UD-070 from Clariant),
- of a $C_{12}$-$C_{14}$ alcohol oxyethylenated with 7 mol of ethylene oxide (Genapol LA-070 from Clariant),
- of a $C_{12}$-$C_{14}$ alcohol oxyethylenated with 9 mol of ethylene oxide (Genapol LA-090 from Clariant),
- of a $C_{12}$-$C_{14}$ alcohol oxyethylenated with 11 mol of ethylene oxide (Genapol LA-110 from Clariant),
- of a $C_{16}$-$C_{18}$ alcohol oxyethylenated with 8 mol of ethylene oxide (Genapol T-080 from Clariant),
- of a $C_{16}$-$C_{18}$ alcohol oxyethylenated with 11 mol of ethylene oxide (Genapol T-110 from Clariant),
- of a $C_{16}$-$C_{18}$ alcohol oxyethylenated with 15 mol of ethylene oxide (Genapol T-150 from Clariant),
- of a $C_{16}$-$C_{18}$ alcohol oxyethylenated with 20 mol of ethylene oxide (Genapol T-200 from Clariant),
- of a $C_{16}$-$C_{18}$ alcohol oxyethylenated with 25 mol of ethylene oxide (Genapol T-250 from Clariant),
- of a $C_{18}$-$C_{22}$ alcohol oxyethylenated with 25 mol of ethylene oxide,
- of a $C_{16}$-$C_{18}$ isoalcohol oxyethylenated with 25 mol of ethylene oxide.

According to one preferred embodiment, the amphiphilic polymer is a copolymer of AMPS and of a $C_{16}$-$C_{18}$ alkyl methacrylate comprising from 6 to 25 mol of oxyethylene groups, obtained from methacrylic acid or a methacrylic acid salt and from a $C_{16}$-$C_{18}$ alcohol oxyethylenated with 6 to 25 mol of ethylene oxide. The amphiphilic polymer may also be a copolymer of AMPS and of a $C_{12}$-$C_{14}$ alkyl methacrylate comprising from 6 to 25 oxyethylene groups, obtained from methacrylic acid or a methacrylic acid salt and from a $C_{12}$-$C_{14}$ alcohol oxyethylenated with 6 to 25 mol of ethylene oxide.

As amphiphilic polymers that are preferred according to the present invention, mention may be made of:
the non-crosslinked copolymer obtained from 92.65 mol % of AMPS and 7.35 mol % of a $C_{16}$-$C_{18}$ alkyl methacrylate comprising 8 oxyethylene groups (Genapol T-080), such as the product sold by the company Clariant under the name Aristoflex SNC;
the non-crosslinked copolymer obtained from 91.5 mol % of AMPS and 8.5 mol % of a $C_{12}$-$C_{14}$ alkyl methacrylate comprising 7 oxyethylene groups (Genapol LA-070), such as the product sold by the company Clariant under the name Aristoflex LNC;
and mixtures thereof.

The amphiphilic polymer(s) as described above are optionally present in the composition according to the invention in a content of between 0.01% and 10% by weight, preferably between 0.05% and 5% by weight, more preferentially between 0.1% and 3% by weight, relative to the total weight of the composition.

Salts of an Ester of Phosphoric Acid and of a Fatty Alcohol

The composition according to the present invention can optionally additionally comprise one or more salts of an ester of phosphoric acid and of a fatty alcohol.

The alkali metal salts of an ester of phosphoric acid and of a fatty alcohol in accordance with the invention correspond to formula (XIII) below:

$$(R'O)\text{—}P(O)\text{—}(O^-M)_2 \qquad (XIII)$$

in which R' represents a linear or branched, saturated $C_8$-$C_{22}$ alkyl group and M represents an alkali metal such as sodium or potassium, and even more preferentially potassium;

R' can denote for example lauryl, cetyl, stearyl and more preferentially cetyl. The salts of an ester of phosphoric acid and of a fatty alcohol can be in the form of a salt of a mixture of esters of phosphoric acid and of a fatty alcohol.

According to one preferred mode of the invention, use will be made of a potassium salt of a mixture of esters of phosphoric acid and of cetyl alcohol, having the INCI name Potassium Cetyl Phosphate, for example the product sold under the trade name Amphisol K® by the company DSM Nutritional Products Inc, or the product sold under the trade name Evermap 160K® by the company Sino Lion (USA) Ltd., or the product sold under the trade name Hostaphat CK 100 ® by the company Clariant International Ltd.

The salt(s) of an ester of phosphoric acid and of a fatty alcohol as described above are optionally present in the composition according to the invention in a content of between 0.1% and 5% by weight, and more preferentially from 0.1% to 3% by weight, relative to the total weight of the composition.

Additives

The composition according to the present invention can optionally also comprise one or more additives, different from the compounds of the invention and normally used in cosmetics, and particularly in the field of anti-sun, care and makeup products, such as alcohols such as ethanol; glycols, such as dipropylene glycol and butylene glycol; glycerol; active agents; salts; organic particles; amphiphilic polymers, such as the Pemulens TR1 or TR2 or Carbopol ETD2020, sold by the company Lubrizol; hydrophilic polymers, such as poly(N-vinylpyrrolidone); polysaccharides, for instance guar gums, xanthan gums and cellulose-based derivatives; water-soluble or water-dispersible silicone derivatives, for instance acrylic silicones, polyether silicones and cationic silicones; and mixtures thereof.

As active agents, mention may in particular be made of vitamins (A, C, E, K, PP, etc), alone or as a mixture, and also derivatives thereof; keratolytic and/or desquamating agents (salicylic acid and derivatives thereof, alpha-hydroxy acids, ascorbic acid and derivatives thereof); depigmenting agents; tensioning agents such as synthetic polymers; plant proteins; polysaccharides of plant origin optionally in the form of microgels; wax dispersions; mixed silicates and colloidal particles of inorganic fillers; matting agents; agents for preventing hair loss and/or hair restorers; or anti-wrinkle agents; and mixtures thereof.

Of course, those skilled in the art will take care to select this or these optional additional compound(s) such that the advantageous properties intrinsically associated with the composition in accordance with the invention are not, or are not substantially, adversely affected by the envisaged addition(s).

The above additives may generally be present in an amount, for each of them, of between 0 and 20% by weight relative to the total weight of the composition.

Forms of the Composition

The compositions according to the invention may be prepared according to the techniques that are well known to those skilled in the art. They may in particular be in the form of a simple or complex emulsion (oil-in-water, or abbreviated to O/W, water-in-oil or W/O, oil-in-water-in-oil or O/W/O, or water-in-oil-in-water or W/O/W), such as a cream, a milk or a cream gel.

When the composition according to the invention is in the form of an oil-in-water emulsion, the composition according to the invention comprises a continuous aqueous phase and at least one oily phase dispersed in the aqueous phase.

When the composition according to the invention is in the form of a water-in-oil emulsion, the composition according to the invention comprises a continuous oily phase and at least one aqueous phase dispersed in the oily phase.

According to the invention, the aqueous phase contains water and optionally other water-soluble or water-miscible organic solvents.

An aqueous phase that is suitable for use in the invention may comprise, for example, a water chosen from a natural spring water, such as water from La Roche-Posay, water from Vittel or waters from Vichy, or a floral water.

The water-soluble or water-miscible solvents that are suitable for use in the invention comprise short-chain monoalcohols, for example $C_2$-$C_4$ monoalcohols, such as ethanol or isopropanol; diols or polyols, such as ethylene glycol, propylene glycol, 1,3-butylene glycol, hexylene glycol, diethylene glycol, dipropylene glycol, propane-1,3-diol, pentylene glycol, caprylyl glycol, 2-ethoxyethanol, diethylene glycol monomethyl ether, triethylene glycol monomethyl ether, glycerol and sorbitol, and mixtures thereof.

According to one preferred embodiment of the invention, use may more particularly be made of ethanol, propylene glycol, glycerol, propane-1,3-diol, and mixtures thereof. In particular, the water may be present in a total quantity ranging from 30 to 99% by weight, preferably from 50 to 99% by weight, and better still from 60 to 98% by weight, relative to the total weight of the aqueous phase.

The water may be present in a total quantity greater than or equal to 30% by weight, preferably greater than or equal to 45% by weight, and preferentially ranges from 45% to 65% by weight, relative to the total weight of composition.

According to the invention, the term "oily phase" is intended to mean a phase comprising at least one oil and all of the liposoluble and lipophilic ingredients and the fatty substances used for the formulation of the compositions of the invention.

The term "oil" is intended to mean any fatty substance that is in liquid form at ambient temperature (25° C.) and at atmospheric pressure ($1.013 \times 10^5$ Pa).

The term "fatty substance" is intended to mean an organic compound that is insoluble in water at ambient temperature (25° C.) and at atmospheric pressure ($1.013 \times 10^5$ Pa) (solubility of less than 5% by weight, preferably less than 1% by weight and even more preferably less than 0.1% by weight). The fatty substances have in their structure at least one hydrocarbon-based chain comprising at least six carbon atoms and/or a sequence of at least two siloxane groups. In addition, the fatty substances are generally soluble in organic solvents under the same temperature and pressure conditions, for instance chloroform, dichloromethane, carbon tetrachloride, ethanol, benzene, toluene, tetrahydrofuran (THF), liquid petroleum jelly or decamethylcyclopentasiloxane.

The oils suitable for the invention may be volatile or non-volatile.

The oils suitable for the invention may be chosen from hydrocarbon-based oils, silicone oils and fluoro oils, and mixtures thereof.

A hydrocarbon-based oil that is suitable for use in the invention may be an animal hydrocarbon-based oil, a plant hydrocarbon-based oil, a mineral hydrocarbon-based oil or a synthetic hydrocarbon-based oil.

An oil that is suitable for use in the invention may be advantageously chosen from mineral hydrocarbon-based oils, plant hydrocarbon-based oils, synthetic hydrocarbon-based oils and silicone oils, and mixtures thereof.

For the purposes of the present invention, the term "silicone oil" means an oil comprising at least one silicon atom, and especially at least one Si—O group.

The term "hydrocarbon-based oil" means an oil mainly containing hydrogen and carbon atoms.

The term "fluoro oil" refers to an oil comprising at least one fluorine atom.

A hydrocarbon-based oil that is suitable for use in the invention may also optionally comprise oxygen, nitrogen, sulfur and/or phosphorus atoms, for example in the form of hydroxyl, amine, amide, ester, ether or acid groups, and in particular in the form of hydroxyl, ester, ether or acid groups.

The oily phase may comprise one or more volatile or non-volatile hydrocarbon-based oils and/or one or more volatile and/or non-volatile silicone oils.

For the purposes of the invention, the term "volatile oil" is intended to mean an oil that is capable of evaporating on contact with the skin or the keratin fibre in less than one hour, at ambient temperature and atmospheric pressure. The volatile oil(s) of the invention are volatile cosmetic oils that are liquid at ambient temperature with a non-zero vapour pressure, at ambient temperature and atmospheric pressure ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" is intended to mean an oil that remains on the skin or the keratin fibre at ambient temperature and atmospheric pressure for at least several hours, and that in particular has a vapour pressure of less than $10^{-3}$ mmHg (0.13 Pa).

Among the non-volatile hydrocarbon-based oils that can be used according to the invention, mention may be made of glyceride triesters and in particular caprylic/capric acid triglycerides such as those sold by the company Stearineries Dubois or those sold under the names Miglyol 810®, 812® and 818® by the company Dynamit Nobel, fatty amides such as isopropyl N-lauroyl sarcosinate, such as the product sold under the trade name Eldew SL 205® from Ajinomoto, synthetic esters, and in particular isononyl isononanoate, diisopropyl sebacate, $C_{12}$-$C_{15}$ alkyl benzoate, such as the product sold under the trade name Finsolv TN® or Witconol TN® by the company Witco or Tegosoft TN® by the company Evonik Goldschmidt, 2-ethylphenylbenzoate, such as the commercial product sold under the name X-Tend 226® by the company ISP, and fatty alcohols, in particular octyldodecanol.

As volatile hydrocarbon-based oils that may be used according to the invention, mention may be made in particular of hydrocarbon-based oils having from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane or isohexadecane, the oils sold under the Isopar or Permethyl trade names, branched $C_8$-$C_{16}$ esters, isohexyl neopentanoate, and mixtures thereof.

Among the non-volatile silicone oils, mention may be made of non-volatile polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Among the volatile silicone oils, mention may for example be made of volatile linear or cyclic silicone oils, in particular those with a viscosity at 25° C. of less than or equal to 8 centistokes ($8\times10^{-6}$ m$^2$/s) and in particular containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Among the volatile fluoro oils, mention may be made of nonafluoromethoxybutane, decafluoropentane, tetradecafluorohexane and dodecafluoropentane, and mixtures thereof.

An oily phase according to the invention may also comprise other fatty substances, mixed with or dissolved in the oil.

Another fatty substance that may be present in the oily phase may be, for example:
- a fatty acid, for example chosen from fatty acids comprising from 8 to 30 carbon atoms, such as lauric acid, palmitic acid, oleic acid and stearic acid;
- a wax chosen from waxes such as lanolin, beeswax, carnauba or candelilla wax, paraffin waxes, lignite waxes, microcrystalline waxes, ceresin or ozokerite, or synthetic waxes, such as polyethylene waxes or Fischer-Tropsch waxes;
- a gum chosen from silicone gums (dimethiconol);
- a pasty compound, such as polymeric or non-polymeric silicone compounds, esters of a glycerol oligomer, arachidyl propionate, fatty acid triglycerides and derivatives thereof;
- and mixtures thereof.

When the composition according to the invention is in the form of an oil-in-water emulsion, the amount of aqueous phase preferably ranges from 50% to 95% by weight, more preferentially from 50% to 90% by weight, even better still from 50% to 80% by weight, and even more preferentially from 55% to 75% by weight, relative to the total weight of the composition.

The amount of oily phase preferably ranges from 5% to 50% by weight and more preferentially from 10% to 45% by weight, relative to the total weight of the composition.

The numerical mean size of the droplets of oil, present in the composition of the invention, preferably ranges from 0.4 to 40 microns and more preferentially from 1 to 20 microns.

This numerical mean size can be measured using a particle size analyser.

When the composition according to the invention is in the form of a water-in-oil emulsion, the amount of oily phase preferably ranges from 50% to 95% by weight, more preferentially from 50% to 90% by weight, even better still from 50% to 80% by weight, and even more preferentially from 55% to 75% by weight, relative to the total weight of the composition.

The amount of aqueous phase preferably ranges from 5% to 50% by weight and more preferentially from 10% to 45% by weight, relative to the total weight of the composition.

The numerical mean size of the droplets of water, present in the composition of the invention, preferably ranges from 0.4 to 40 microns and more preferentially from 1 to 20 microns.

This numerical mean size can be measured using a particle size analyser.

In the case of compositions in the form of oil-in-water or water-in-oil emulsions, the emulsification processes that may be used are of the paddle or impeller, rotor-stator and HHP (high hydrostatic pressure) type.

In order to obtain stable emulsions with a low content of polymer (oil/polymer ratio >25), it is possible to prepare the dispersion in concentrated phase and then to dilute the dispersion with the remainder of the aqueous phase.

The emulsions generally contain at least one emulsifier chosen from amphoteric, anionic, cationic or non-ionic surfactants as described above, used alone or as a mixture. The emulsifiers are chosen in an appropriate manner according to the emulsion to be obtained (W/O or O/W emulsion).

When it is an emulsion, the aqueous phase of this emulsion may comprise a non-ionic vesicular dispersion prepared according to known processes (Bangham, Standish and Watkins, J. Mol. Biol. 13, 238 (1965), FR 2 315 991 and FR 2 416 008).

The compositions according to the invention may also be in the form of an anhydrous composition, for instance in the form of an oil. The term "anhydrous composition" is intended to mean a composition containing less than 2% by weight of water, preferably less than 1% by weight of water, and even more preferentially less than 0.5% by weight of water relative to the total weight of the composition, or even a composition that is free of water. In compositions of this type, the water possibly present is not added during the preparation of the composition, but corresponds to the residual water provided by the mixed ingredients. They may optionally be packaged in aerosol form and may be in the form of a mousse or a spray.

The anhydrous compositions according to the invention comprise at least one oil, preferably chosen from those described above, and more preferentially chosen from hydrocarbon-based oils, silicone oils, fluoro oils, and/or mixtures thereof.

According to one preferred embodiment of the invention, the composition according to the invention comprises at least one oil chosen from hydrocarbon-based oils, silicone oils, fluoro oils, and/or mixtures thereof.

According to a first variant of this preferred embodiment, the composition according to the invention is in the form of an oil-in-water or water-in-oil emulsion, preferentially in the form of an oil-in-water emulsion.

According to a second variant of this preferred embodiment, the composition according to the invention is in the form of an anhydrous composition.

The cosmetic compositions according to the invention may have a liquid to semi-liquid consistency, such as milks, more or less smooth creams, cream gels, or pastes. They may optionally be packaged in aerosol form and may be in the form of a mousse or a spray.

The compositions according to the invention in the form of vapourizable fluid lotions in accordance with the invention are applied to the skin or hair in the form of fine particles by means of pressurizing devices. The devices in accordance with the invention are well known to those skilled in the art and comprise non-aerosol pumps or "atomizers", aerosol containers comprising a propellant and aerosol pumps using compressed air as propellant. These devices are described in U.S. Pat. Nos. 4,077,441 and 4,850,517.

The compositions packaged in aerosol form in accordance with the invention generally contain conventional propellants, for instance hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

The cosmetic compositions according to the invention may be used as care products and/or anti-sun protection products for the face and/or the body.

A subject of the present invention is also a cosmetic method for treating the skin, in particular human skin, against UV radiation, comprising at least one step of applying to the skin a composition as defined previously.

A subject of the present invention is also the use of at least one compound capable of accepting the triplet excited level energy of said dibenzoylmethane derivative compound(s) as defined previously, for photostabilizing with respect to UV radiation, a composition comprising at least one dibenzoylmethane derivative compound (i) as defined previously and at least one merocyanine compound (ii) as defined previously; preferably, the UV radiation corresponds to solar radiation.

A subject of the present invention is also a composition as defined previously, for use in a method for protecting the skin against UV radiation, in particular against solar radiation.

The examples that follow serve to illustrate the invention without, however, being limiting in nature.

EXAMPLES

The compositions 1, 2 and 3 are prepared from the ingredients shown in the table below, the amounts of which are expressed as weight percentages of active material (AM).

| Phases | Ingredients | Composition 1 (Comparative) | Composition 2 (Invention) | Composition 3 (Invention) |
|---|---|---|---|---|
| A | Water | qs | qs | qs |
|  | Glycerol | 5 | 5 | 5 |
|  | Triethanolamine | 0.45 | 0.45 | 0.45 |
|  | Disodium EDTA | 0.1 | 0.1 | 0.1 |
|  | Preservative | qs | qs | qs |
|  | Ammonium acryloyldimethyltaurate/ Steareth-8 MethacrylatE Copolymer (ARISTOFLEX SNC ®) | 0.5 | 0.5 | 0.5 |
| B | Isopropyl Lauroyl Sarcosinate | 30 | 30 | 30 |
|  | 4-tert-butyl-4'-methoxydibenzoylmethane | 2 | 2 | 2 |
|  | 2-ethoxyethyl 2-cyano{3-[(3-methoxypropyl)amino]cyclohex-2-en-1-ylidene}ethanoate | 1 | 1 | 1 |
|  | Diethylhexyl syringylidenemalonate + 90/10 Caprylic/Capric Triglyceride (OXYNEX ST LIQUID) | — | 2 | — |
|  | Tris(Tetramethylhydroxypiperidinol) Citrate (TINOGARD QS) | — | — | 0.01 |

-continued

| Phases | Ingredients | Composition 1 (Comparative) | Composition 2 (Invention) | Composition 3 (Invention) |
|---|---|---|---|---|
| | Stearyl Alcohol | 1 | 1 | 1 |
| | Glyceryl Isostearate | 0.5 | 0.5 | 0.5 |
| C | Isohexadecane | 1 | 1 | 1 |
| | Xanthan gum | 0.2 | 0.2 | 0.2 |
| | Ammonium Polyacryloyldimethyl Taurate (HOSTACERIN AMPS ®) | 0.4 | 0.4 | 0.4 |

Composition Preparation Method:

The aqueous phase A and the oily phase B were prepared by mixing the starting materials with mechanical stirring at 80° C. Once the aqueous phase A and the oily phase B are macroscopically homogeneous, the emulsion is prepared by introducing the phase B into the phase A with stirring by means of a rotor-stator homogenizer at a stirring speed of 4500 revolutions per minute for 20 minutes. The phase C is then added, and the composition is called to ambient temperature (25° C.).

Results:

Once the compositions 1 to 3 have been prepared, these are then irradiated under a UV-A sun lamp at 21.6 J/cm$^2$, for one hour.

After irradiation, the residual contents of the compounds 4-tert-butyl-4'-methoxydibenzoylmethane and 2-ethoxyethyl 2-cyano {3-[(3-methoxypropyl)amino]-cyclohex-2-en-1-ylidene}ethanoate in each of the compositions were measured by conventional HPLC chromatography methods.

The residual content of the ingredient corresponds to the weight ratio of the content of the ingredient after UV irradiation to the content of the ingredient before UV irradiation. The residual contents are expressed as percentages.

The results obtained are collated in the table below:

| Residual contents after irradiation | Composition 1 (Comparative) | Composition 2 (Invention) | Composition 3 (Invention) |
|---|---|---|---|
| 4-tert-butyl-4'-methoxydibenzoylmethane | 72% | 86% | 87% |
| 2-ethoxyethyl 2-cyano{3-[(3-methoxypropyl)amino]cyclohex-2-en-1-ylidene}ethanoate | 46% | 72% | 71% |

These results show that the compositions 2 and 3 according to the invention exhibit residual contents of the dibenzoylmethane derivative and of the merocyanine compound that are substantially higher compared with the comparative composition 1, and thus exhibit better photostability with respect to UV radiation.

The invention claimed is:

1. Photoprotective composition for topical use, characterized in that it comprises, in a cosmetically acceptable medium:
   (i) from 0.3% to 10% by weight of 4-tert-butyl-4'-methoxydibenzoylmethane, relative to the total weight of the composition;
   (ii) from 0.3% to 10% of 2-ethoxyethyl 2-cyano{3-[(3-methoxypropyl)amino]cyclohex-2-en-1-ylidene}ethanoate, relative to the total weight of the composition; and
   (iii) from 0.001% to 10% by weight, relative to the total weight of the composition, of at least one compound capable of accepting the triplet excited level energy of 4-tert-butyl-4'-methoxydibenzoylmethane chosen from diethylhexyl syringylidenemalonate or tris(tetramethylhydroxypiperidinol) citrate.

2. Composition according to claim 1, characterized in that the total content of 4-tert-butyl-4'-methoxydibenzoylmethane (i) is between 0.3% and 5% by weight, relative to the total weight of the composition.

3. Composition according to claim 1, characterized in that the total content of 2-ethoxyethyl 2-cyano{3-[(3-methoxypropyl)amino]cyclohex-2-en-1-ylidene}ethanoate (ii) is between 0.3% and 5% by weight, relative to the total weight of the composition.

4. Composition according to claim 1, characterized in that the total content of the compound(s) (iii) capable of accepting the triplet excited level energy of 4-tert-butyl-4'-methoxydibenzoylmethane chosen from diethylhexyl syringylidenemalonate or tris(tetramethylhydroxypiperidinol) citrate is between 0.005% and 5% by weight, relative to the total weight of the composition.

5. Composition according to claim 1, characterized in that the ratio of the weight content of the compound(s) (iii) capable of accepting the triplet excited level energy of 4-tert-butyl-4'-methoxydibenzoylmethane chosen from diethylhexyl syringylidenemalonate or tris(tetramethylhydroxypiperidinol) citrate to the sum of the weight contents of 4 tert-butyl-4'-methoxydibenzoylmethane (i) and of 2 ethoxyethyl 2-cyano{3-[(3-methoxypropyl)amino]cyclohex-2-en-1-ylidene}ethanoate (ii), is between 0.01 and 20.

6. Composition according to claim 1, characterized in that it also comprises one or more additional UV-screening agents chosen, alone or as a mixture, from anthranilates; salicylic derivatives; benzylidenecamphor derivatives; benzophenone derivatives; β,β-diphenylacrylate compounds different from ethylhexyl methoxycrylene derivatives; triazine derivatives; benzotriazole derivatives; benzalmalonate derivatives; benzimidazole derivatives; imidazolines; bisbenzoazolyl derivatives; p-aminobenzoic acid (PABA) derivatives; methylenebis(hydroxyphenyl benzotriazole) derivatives; benzoxazole derivatives; screening polymers and screening silicones; α-alkylstyrene-based dimers; 4,4-diarylbutadienes; and/or treated or untreated metal oxide pigments or nanopigments, and mixtures thereof.

7. Composition according to claim 6, in which the additional UV-screening agents are chosen, alone or as a mixture, from the following UV-screening agents: ethylhexyl salicylate, octocrylene, phenylbenzimidazole sulfonic acid, benzophenone-3, benzophenone-4, benzophenone-5, n-hexyl 2-(4-diethylamino-2-hydroxybenzoyl)benzoate, 4-methylbenzylidenecamphor, terephthalylidenedicamphorsulfonic acid, disodium phenyldibenzimidazole tetrasulfonate, methylenebisbenzotriazolyl tetramethylbutylphenol, ethylhexyl triazone, diethylhexyl butamido triazone, drometrizole trisiloxane, polysilicone-15, 1,1-dicarboxy(2,2'-dimethylpropyl)-4,4-diphenylbutadiene, 2,4-bis[5-1-(dimethylpropyl)benzoxazol-2-yl(4-phenyl)imino]-6-(2-ethylhexyl)imino-1,3,5-triazine, and mixtures thereof.

8. Composition according to claim 1, characterized in that it comprises at least one oil chosen from hydrocarbon-based oils, silicone oils, fluoro oils, and/or mixtures thereof.

9. Composition according to claim 1, characterized in that it is in the form of an oil-in-water or water-in-oil emulsion.

10. Cosmetic method for treating the skin against UV radiation, comprising at least one step of applying to the skin a composition as defined in claim 1.

11. A method of photostabilizing a composition comprising 4-tert-butyl-4'-methoxydibenzoylmethane and 2-ethoxyethyl 2-cyano{3-[(3-methoxypropyl)amino]cyclohex-2-en-1-ylidene}ethanoate, with respect to UV radiation, (ii) the method comprising adding to the composition at least one compound capable of accepting the triplet excited level energy of 4-tert-butyl-4'-methoxydibenzoylmethane chosen from diethylhexyl syringylidenemalonate or tris(tetramethylhydroxypiperidinol) citrate, wherein the total content of 4-tert-butyl-4'-methoxydibenzoylmethane is between 0.3% and 10% by weight, relative to the total weight of the composition, wherein the total content of 2-ethoxyethyl 2-cyano{3-[(3-methoxypropyl)amino]cyclohex-2-en-1-ylidene}ethanoate is between 0.3% and 10% by weight, relative to the total weight of the composition and wherein the total content of diethylhexyl syringylidenemalonate or tris(tetramethylhydroxypiperidinol) citrate is between 0.001% and 10% by weight, relative to the total content of the composition.

* * * * *

UNITED STATES PATENT AND TRADEMARK OFFICE
CERTIFICATE OF CORRECTION

PATENT NO. : 11,344,487 B2
APPLICATION NO. : 16/627177
DATED : May 31, 2022
INVENTOR(S) : A. Batista et al.

It is certified that error appears in the above-identified patent and that said Letters Patent is hereby corrected as shown below:

In the Claims

| Column | Line | |
|---|---|---|
| 40 | 4 | change "(ii) the" to -- the --. |

Signed and Sealed this
Twentieth Day of December, 2022

Katherine Kelly Vidal
*Director of the United States Patent and Trademark Office*